(12) United States Patent
Toji

(10) Patent No.: US 10,722,215 B2
(45) Date of Patent: Jul. 28, 2020

(54) ULTRASOUND DIAGNOSTIC DEVICE AND ULTRASOUND DIAGNOSTIC DEVICE CONTROL METHOD

(71) Applicant: KONICA MINOLTA, INC., Chiyoda-ku, Tokyo (JP)

(72) Inventor: Bumpei Toji, Hashima (JP)

(73) Assignee: KONICA MINOLTA, INC., Tokyo (JP)

( * ) Notice: Subject to any disclaimer, the term of this patent is extended or adjusted under 35 U.S.C. 154(b) by 468 days.

(21) Appl. No.: 15/160,569

(22) Filed: May 20, 2016

(65) Prior Publication Data

US 2016/0345939 A1 Dec. 1, 2016

(30) Foreign Application Priority Data

May 27, 2015 (JP) .................. 2015-107412

(51) Int. Cl.
*A61B 8/08* (2006.01)
*A61B 8/00* (2006.01)

(52) U.S. Cl.
CPC .............. *A61B 8/485* (2013.01); *A61B 8/469* (2013.01); *A61B 8/5207* (2013.01);
(Continued)

(58) Field of Classification Search
CPC ....... A61B 8/485; A61B 8/469; A61B 8/5207; A61B 8/5269; A61B 8/4483; A61B 8/461; A61B 8/54
See application file for complete search history.

(56) References Cited

U.S. PATENT DOCUMENTS

| 5,810,731 A | * | 9/1998 | Sarvazyan | ............... A61B 8/08 600/438 |
| 8,343,050 B2 | | 1/2013 | Fan et al. | |

(Continued)

FOREIGN PATENT DOCUMENTS

| JP | 2010259806 A | 11/2010 |
| JP | 2014028029 A | 2/2014 |

(Continued)

OTHER PUBLICATIONS

Japanese Office Action (and English language translation thereof) dated Apr. 24, 2018 issued in counterpart Japanese Application No. 2015-107412.

*Primary Examiner* — Hien N Nguyen
(74) *Attorney, Agent, or Firm* — Holtz, Holtz & Volek PC

(57) ABSTRACT

An ultrasound diagnostic device that transmits a push pulse in order to detect shear waves, including a push pulse transmitter, a displacement detector, an evaluator, and a push pulse adjuster. The push pulse transmitter transmits the push pulse based on a transmission profile. The displacement detector repeatedly transmits ultrasound into the subject after the push pulse, receives reflected ultrasound from the subject that corresponds to transmitted ultrasound, and detects displacement due to shear waves caused by the push pulse. The evaluator evaluates shear wave propagation based on detected displacement. The push pulse adjuster adjusts the transmission profile based on evaluation results. When the transmission profile is adjusted, the push pulse transmitter transmits a second push pulse based on the adjusted transmission profile and the displacement detector detects displacement caused by the second push pulse.

14 Claims, 12 Drawing Sheets

(52) U.S. Cl.
CPC ............. *A61B 8/4483* (2013.01); *A61B 8/461* (2013.01); *A61B 8/5269* (2013.01); *A61B 8/54* (2013.01)

(56) References Cited

U.S. PATENT DOCUMENTS

| | | | |
|---|---|---|---|
| 9,072,493 B1 | 7/2015 | Yoshikawa | |
| 2004/0167403 A1* | 8/2004 | Nightingale | A61B 5/0053 600/437 |
| 2013/0131511 A1* | 5/2013 | Peterson | A61B 5/0048 600/438 |
| 2015/0005633 A1 | 1/2015 | Kanayama et al. | |
| 2015/0080730 A1* | 3/2015 | Kanayama | A61B 8/5207 600/447 |
| 2015/0133782 A1 | 5/2015 | Yoshikawa | |
| 2015/0164480 A1* | 6/2015 | Watanabe | A61B 8/463 600/438 |
| 2015/0173720 A1 | 6/2015 | Yoshikawa | |

FOREIGN PATENT DOCUMENTS

| | | |
|---|---|---|
| JP | 2015009040 A | 1/2015 |
| JP | 2015023913 A | 2/2015 |
| JP | 2015092938 A | 5/2015 |

\* cited by examiner

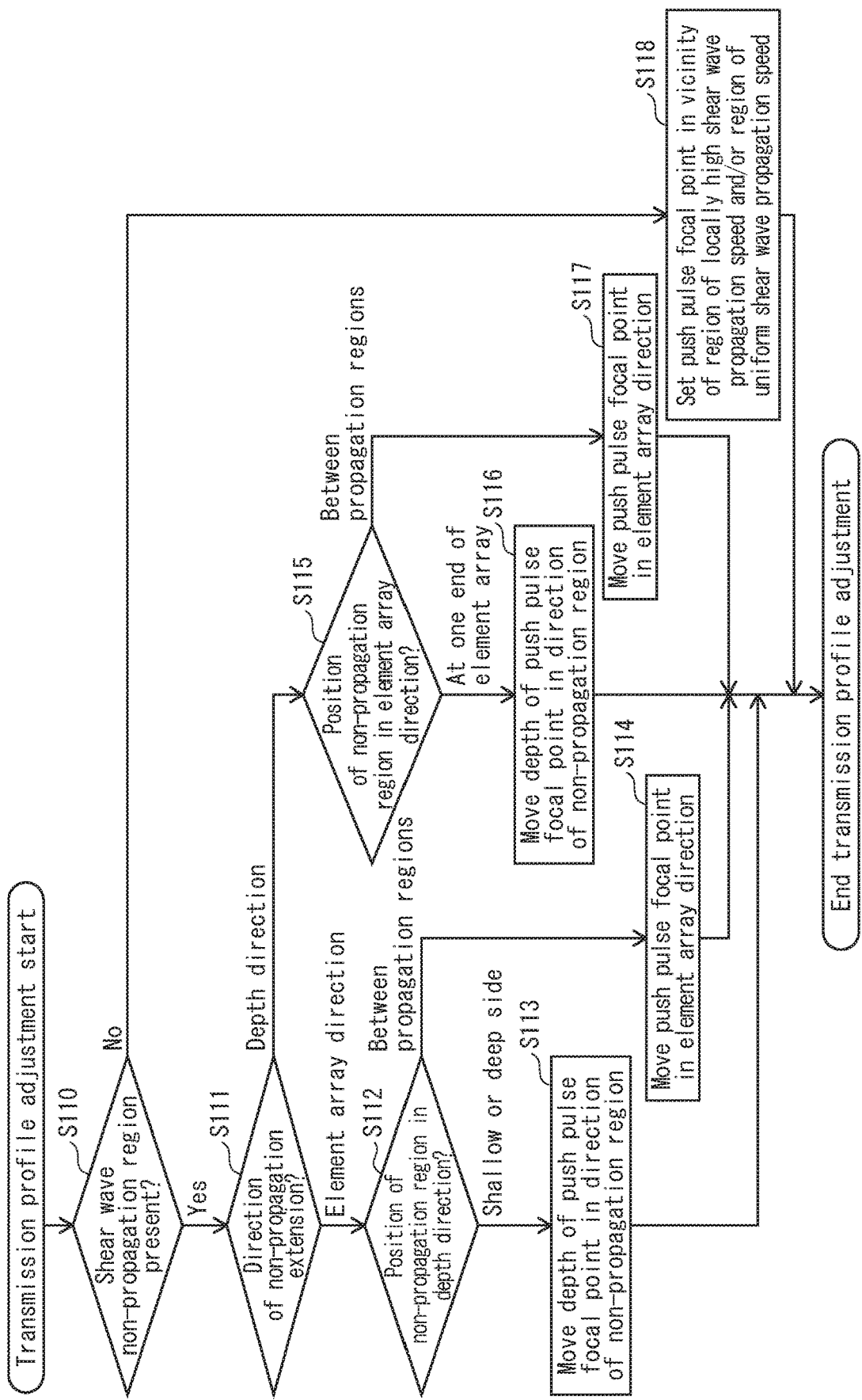

ULTRASOUND DIAGNOSTIC DEVICE AND ULTRASOUND DIAGNOSTIC DEVICE CONTROL METHOD

This application is based on an application No. 2015-107412 filed in Japan on May 27, 2015, the contents of which are hereby incorporated by reference.

BACKGROUND OF THE INVENTION (1) Field of the Invention

The present disclosure relates to imaging processing of ultrasound diagnostic devices, and in particular to hardness measurement of tissue using shear waves.

(2) Description of the Related Art

In recent years, ultrasound diagnostic devices that have a function of evaluating tissue hardness in a subject have become more prevalent. Methods of evaluating hardness using ultrasound diagnostic devices are broadly divided into two types. One type is a method of evaluating relative hardness of tissue in a subject from magnitude of distortion of the tissue with respect to pressure and a subsequent release of the pressure, the pressure being applied by using an ultrasound probe. This type of method can evaluate relative hardness in a subject, i.e., whether tissue is harder or softer than surrounding tissue.

The other type is a method of generating a shear wave in a region of interest (ROI) in a subject, and measuring propagation speed of the shear wave by acquiring displacement of tissue over a time series in the ROI. Because propagation speed of a shear wave changes according to elastic modulus, this method can evaluate absolute hardness of tissue (for example, elastic modulus). As a method of generating a shear wave, for example, acoustic radiation force impulse (ARFI) is used. Acoustic pressure of an ultrasound push pulse is focused on a focus point, and tissue at the focus point is thereby displaced.

SUMMARY OF THE INVENTION

Problems to be Solved by the Invention

However, when using shear waves, accuracy of shear wave speed detection decreases when displacement of tissue by the shear wave is small, and therefore accuracy of tissue hardness measurement decreases. For example, in situations such as when hard tissue is present at the focus point to which push pulses are transmitted, attenuation or reflection of shear waves may occur, strength of shear waves may be insufficient to generate tissue displacement, and regions that are hard for shear waves to reach may occur. Further, acoustic pressure of push pulses has upper limits according to the properties of ultrasound probes and in view of other effects on tissue. Thus, measurement accuracy may decrease according to the structure of a measurement subject. When accuracy of tissue hardness measurement in a subject decreases, or when measurement fails, an operator needs to guess the cause in order to re-take measurements, and adjust a transmission profile by trial-and-error.

The present disclosure is achieved in view of the problems described above, and has an aim of increasing accuracy of tissue hardness measurement in a way that is easy for an operator.

Means for Solving the Problems

The ultrasound diagnostic device pertaining to one aspect of the present disclosure is an ultrasound diagnostic device that uses an ultrasound probe to transmit a push pulse of focused ultrasound to a focal point in a subject to physically push tissue at the focal point, after which the ultrasound probe is used to repeatedly transmit and receive ultrasound to detect propagation, in a region of interest (ROI), of shear waves that originate from the pushed tissue at the focal point, the ultrasound diagnostic device comprising: an ultrasound signal processing circuit, the ultrasound signal processing circuit comprising: a push pulse transmitter that transmit the push pulse based on a transmission profile; a displacement detector that repeatedly transmits ultrasound into the subject after the push pulse, receives reflected ultrasound from the subject that corresponds to transmitted ultrasound in order to acquire a time series of receive signals, and detects displacement due to shear waves in tissue in the ROI that are caused by the push pulse; an evaluator that evaluates shear wave propagation in the ROI, based on detection results from the displacement detector; and a push pulse adjuster that adjusts the transmission profile, based on evaluation results from the evaluator, wherein when the push pulse adjuster adjusts the transmission profile, the push pulse transmitter transmits a second push pulse based on the adjusted transmission profile, and the displacement detector detects displacement due to shear waves that are caused by the second push pulse.

BRIEF DESCRIPTION OF THE DRAWINGS

These and the other objects, advantages and features of the invention will become apparent from the following description thereof taken in conjunction with the accompanying drawings which illustrate a specific embodiment of the invention. In the drawings:

FIG. 7 is a flowchart showing push pulse transmission profile adjustment pertaining to the embodiment;

DESCRIPTION OF EMBODIMENT

Developments that led to the Embodiment of the Present Invention

The inventors investigated various ways to improve measurement accuracy in ultrasound diagnostic devices that use shear waves to perform tissue hardness measurement.

As stated above, shear wave propagation speed changes according to elasticity of tissue. Thus, in order to increase accuracy of tissue hardness measurement, accurate calculation of shear wave propagation speed is required. Thus, it is desirable that tissue displacement due to shear waves is great, and that shear waves propagate throughout a region of interest (ROI) without attenuation. However, when considering other effects on tissue, it is not desirable to generate tissue displacement any greater than required. Accordingly, it is desirable to increase displacement to a maximum within a range that does not have adverse effects on tissue, in order to increase accuracy of tissue hardness measurement without imposing a burden on the subject.

Further, when tissue hardness is not uniform, such as when a plurality of tissues of different hardness are present in the ROI, reflection and refraction of shear waves may occur in locations where hardness varies, for example at tissue boundaries. In such a case, travel direction of a shear wave may change and a travelling wave and a reflected wave may interfere with each other, and therefore accuracy of calculation of shear wave speed may be reduced or calculation may become impossible.

It is difficult to deal with such problems prior to performing tissue hardness measurement. This is because attenuation, reflection, refraction, etc., of shear waves depends on hardness of the tissue. For example, as disclosed in JP 2015-23913, determination of whether or not an ROI is appropriate can be performed based on an ultrasound image (B-mode image), but adjustment of a push pulse transmission profile is performed by an operator by trial-and-error, based on ultrasound images (B-mode images) and results of tissue hardness measurement.

In view of the above technical problems, the inventors investigated techniques for improving push pulse transmission profiles and accuracy of tissue hardness measurement, and arrived at an invention corresponding to the ultrasound diagnostic device pertaining to the present embodiment.

The following describes in detail the ultrasound diagnostic device pertaining to the present embodiment, with reference to the drawings.

Embodiment

Figure 1:
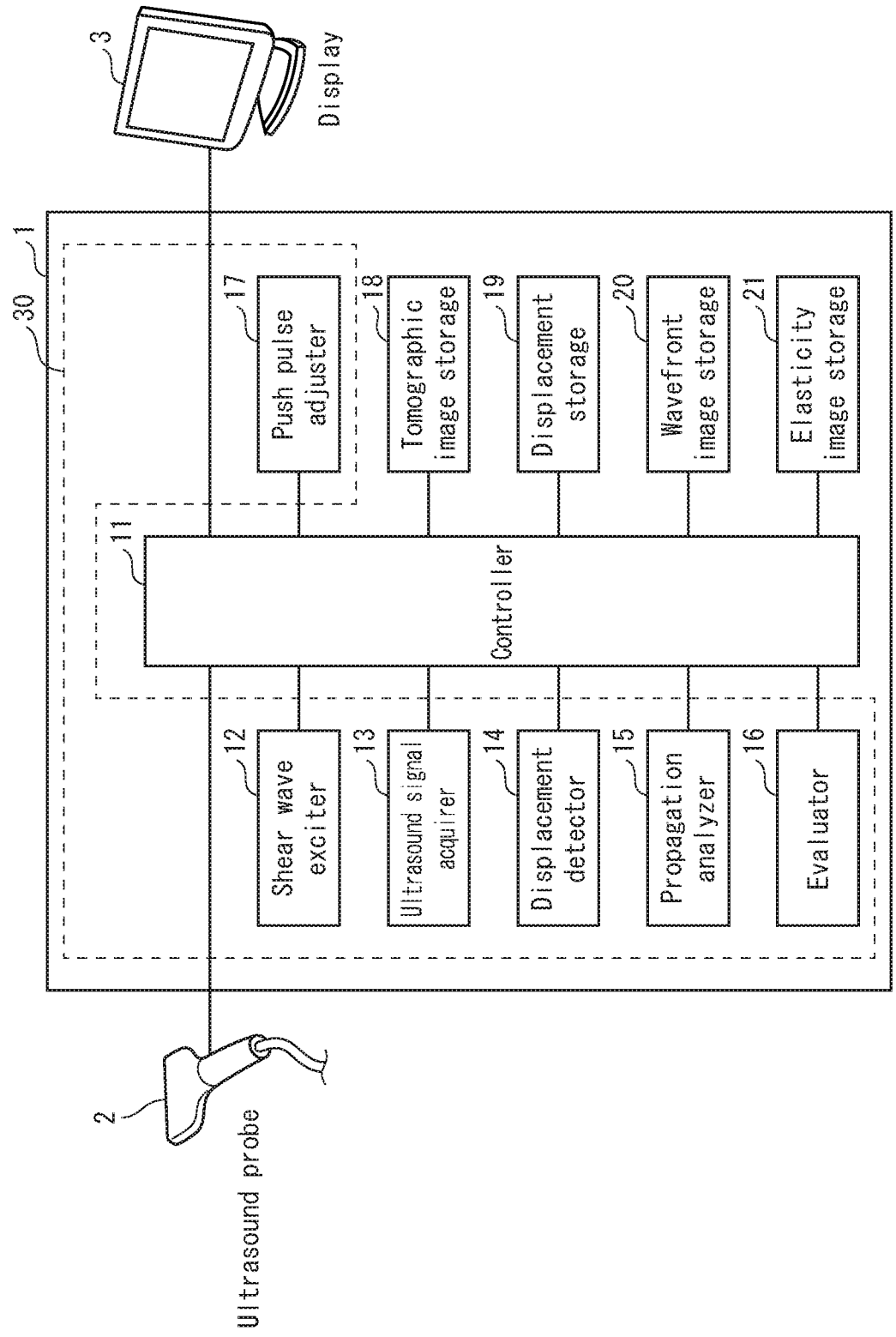
FIG. 1 is a block diagram of an ultrasound diagnostic device 1 pertaining to an embodiment.

A block diagram of an ultrasound diagnostic device 1 pertaining to the present embodiment is illustrated in FIG. 1. The ultrasound diagnostic device 1 comprises a controller 11, a shear wave exciter 12, an ultrasound signal acquirer 13, a displacement detector 14, a propagation analyzer 15, an evaluator 16, a push pulse adjuster 17, a tomographic image storage 18, a displacement amount storage 19, a wavefront image storage 20, and an elasticity image storage 21. Of these, the shear wave exciter 12, the ultrasound signal acquirer 13, the displacement detector 14, the propagation analyzer 15, the evaluator 16, and the push pulse adjuster 17 are elements of an ultrasound signal processing circuit 30. Further, the controller 11 is connectable to an ultrasound probe 2 and a display 3. FIG. 1 shows the ultrasound diagnostic device 1 connected to the ultrasound probe 2 and the display 3.

The ultrasound probe 2, for example, has ultrasound transducers disposed in a linear array (not illustrated). Each transducer, for example, comprises lead zirconate titanate (PZT). The ultrasound probe 2 receives an electric signal generated by the shear wave exciter 12 (hereinafter, "acoustic radiation force impulse (ARFI) drive signal") or an electric signal generated by the ultrasound signal acquirer 13 (hereinafter, "transmission drive signal"), and converts the electric signal received into ultrasound. The ultrasound probe 2, in a state in which a transducer-side outer surface of the ultrasound probe 2 is in contact with a surface such as a skin surface of a subject, converts an ARFI drive signal or transmission drive signal into ultrasound and transmits an ultrasound beam composed of a plurality of ultrasound waves emitted from the plurality of transducers towards a measurement object in the subject. Subsequently, the ultrasound probe 2 receives a plurality of reflected ultrasound waves from the measurement object in response to transmission ultrasound based on transmission drive signals, a plurality of transducers convert the reflected ultrasound waves into electric signals (hereinafter, "transducer-received signals"), and the transducer-received signals are provided to the ultrasound signal acquirer 13 via the controller 11. Note that although the shear wave exciter 12 and the ultrasound signal acquirer 13 are described as separate elements, the shear wave exciter 12 and the ultrasound signal acquirer 13 may be integrated, and transmission drive signals and ARFI drive signals may thereby be generated by the same unit.

The shear wave exciter 12 generates an ARFI drive signal that is an electric signal for causing output of a push pulse by the ultrasound probe 2. Here, "push pulse" means pulsed ultrasound for causing displacement of tissue in a subject in order to generate shear waves in the subject. Specifically, a push pulse is a number of ultrasound waves greater than a number of ultrasound waves in transmission ultrasound, described later, all of which are focused on one point in an ROI in a subject. Accordingly, an ARFI drive signal is a pulsed electric signal that causes ultrasound outputted by the transducers of the ultrasound probe 2 to be generated so that the ultrasound arrives at a focal point. The shear wave exciter 12 receives a transmission profile from the controller 11. The transmission profile defines parameters such as number of consecutive push pulse transmissions, push pulse focal point location, transducers used in transmission, number of waves, and transmission length. Based on the transmission profile, the shear wave exciter 12 generates one or more ARFI drive signals.

The ultrasound signal acquirer 13 generates a transmission drive signal, which is an electric signal for causing the ultrasound probe 2 to transmit transmission ultrasound. The transmission drive signal is a pulsed electric signal with a different timing for each transducer, causing transmission ultrasound transmitted from the transducers of the ultrasound probe 2 to be generated so as to simultaneously arrive at a transmission focus point. Further, the ultrasound signal acquirer 13 performs delay-and-sum on transducer receive signals based on reflected ultrasound, in order to generate an acoustic line signal. The ultrasound signal acquirer 13 outputs a generated acoustic line signal to the tomographic image storage 18 via the controller 11.

The displacement detector 14 acquires, from the tomographic image storage 18 via the controller 11, a plurality of acoustic line signals pertaining to one tomographic image used for displacement detection (hereinafter, "tomographic image signals") and a plurality of acoustic line signals pertaining to one tomographic image used for reference (hereinafter, "reference tomographic image signals"). The reference tomographic image signals are used to extract displacement by shear waves from tomographic image signals, and are specifically tomographic image signals captured from the ROI prior to push pulse transmission. Thus, the displacement detector 14 detects displacement of each pixel represented in a tomographic image signal from differences between tomographic image signals and reference tomographic image signals, and associates displacement with coordinates of each pixel to generate a displacement image. The displacement detector 14 outputs a generated displacement image to the displacement amount storage 19 via the controller 11.

The propagation analyzer 15 acquires a displacement image from the displacement amount storage 19 via the controller 11. The propagation analyzer 15 detects position, travel direction, and speed of a wavefront of a shear wave at each time acquired from displacement images, and generates wavefront images. The propagation analyzer 15 calculates elastic modulus of subject tissue corresponding to each pixel of displacement images from the position, travel direction, and speed of the wavefront of the shear wave, and generates elasticity images. The propagation analyzer 15 outputs, via the controller 11, generated wavefront images to the wavefront image storage 20 and generated elasticity images to the elasticity image storage 21.

The evaluator 16 acquires a wavefront image from the wavefront image storage 20 via the controller 11. The evaluator 16 evaluates, for example, presence or absence of shear wave propagation in an ROI, uniformity of shear wave propagation, and presence or absence of shear wave reflection and refraction, based on the position, travel direction, and speed of a wavefront of a shear wave. The evaluator 16 outputs evaluation results to the controller 11. Details are provided later.

The push pulse adjuster 17 acquires evaluation results outputted by the evaluator 16, via the controller 11. The push pulse adjuster 17 optimizes a push pulse transmission profile, based on evaluation results, and outputs an optimized transmission profile to the controller 11. Details are provided later.

The controller 11, in addition to controlling the elements stated above, outputs an elasticity image generated by the propagation analyzer 15 to the display 3.

The tomographic image storage 18, the displacement amount storage 19, the wavefront image storage 20, and the elasticity image storage 21 store tomographic image data, displacement image data, wavefront image data, and elasticity image data, respectively. The tomographic image storage 18, the displacement amount storage 19, the wavefront image storage 20, and the elasticity image storage 21 are implemented by one or more storage mediums such as RAM, flash memory, a hard disk, an optical disk, etc. Note that two or more of the tomographic image storage 18, the displacement amount storage 19, the wavefront image storage 20, and the elasticity image storage 20 may be implemented by a single storage medium. Further, one or more of the tomographic image storage 18, the displacement amount storage 19, the wavefront image storage 20, and the elasticity image storage 21 may be outside the ultrasound diagnostic device 1 and connectable to the ultrasound diagnostic device 1 via an interface, and may be a resource accessible to the ultrasound diagnostic device 1 via a network, such as a file server or network attached storage (NAS).

The controller 11, the shear wave exciter 12, the ultrasound signal acquirer 13, the displacement detector 14, the propagation analyzer 15, the controller 16, and the push pulse adjuster 17 may each be implemented by hardware such as a field programmable gate array (FPGA) or an application specific integrated circuit (ASIC). Note that a portion or all of the above may be implemented as a single FPGA or ASIC. Further, each of the above may be individually implemented as memory, software, and a programmable device such as a central processing unit (CPU) or graphic processing unit (GPU). Further, two or more of the above may be implemented as memory, software, and a programmable device such as a central processing unit (CPU) or graphics processing unit (GPU).

<Operations>

Figure 2:
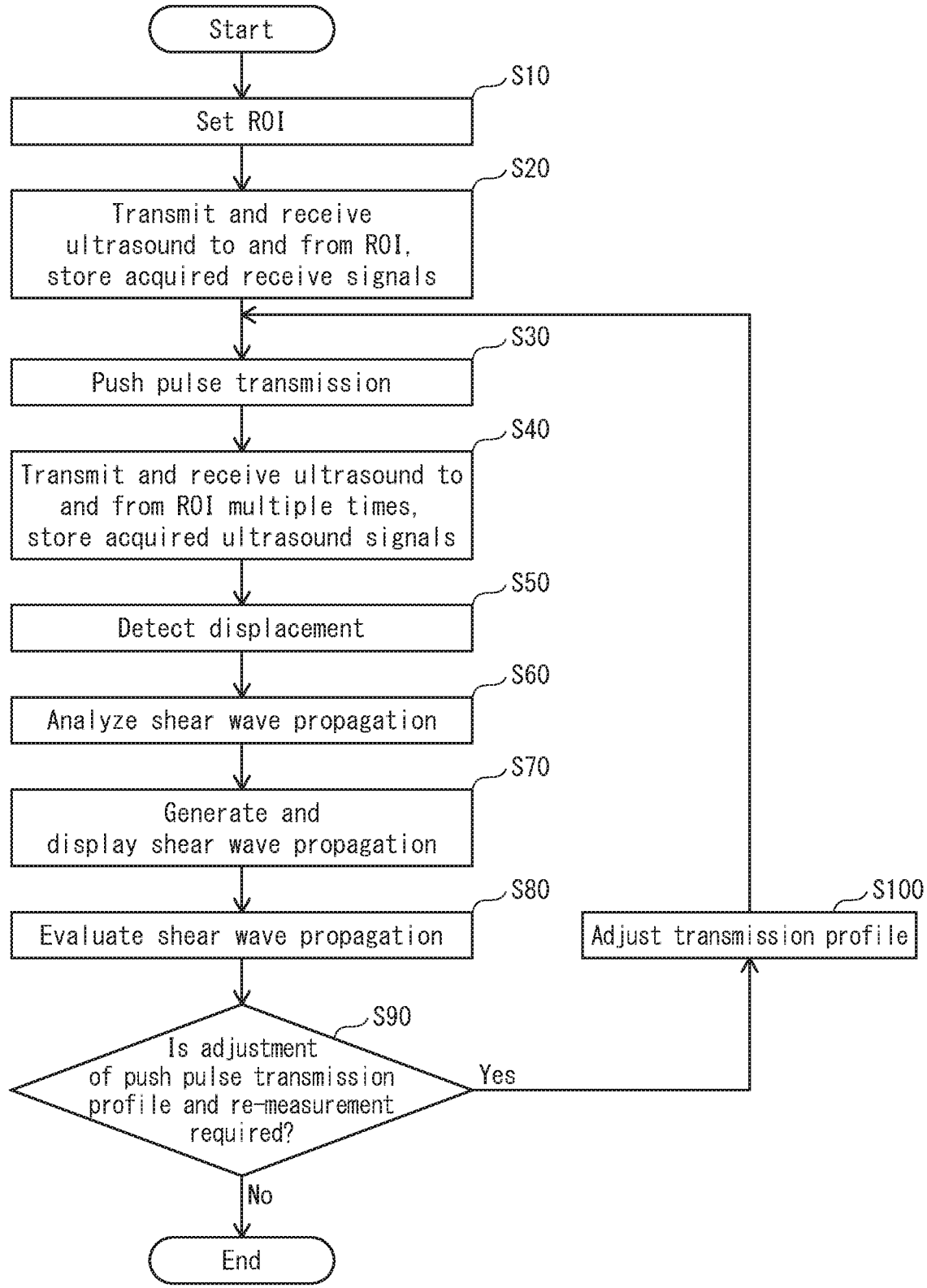
FIG. 2 is a flowchart indicating overall operation of the ultrasound diagnostic device 1 pertaining to the embodiment.

The following describes operation of the ultrasound diagnostic device 1 pertaining to the present embodiment. FIG. 2 is a flowchart illustrating overall operation of the ultrasound diagnostic device 1.

First, the controller 11 sets an ROI in a subject (step S10). Methods of setting an ROI include, for example, displaying the most recent tomographic image stored in the tomographic image storage 18 on the display 3, and an operator specifying the ROI by using an input (not illustrated) such as a touch panel, mouse, or track ball. Methods of setting an ROI are not limited to this example, and all of a tomographic image may be set as an ROI, or a range including a central portion of a tomographic image may be set as an ROI. Further, when setting an ROI, a tomographic image may be acquired.

Subsequently, ultrasound is transmitted to and received from the ROI, and acquired receive signals are stored (step S20). Specifically, the following operations are performed. First, the following transmission event is performed. Initially, the ultrasound signal acquirer 13 generates a pulsed transmit signal. Subsequently, the ultrasound signal acquirer 13 performs transmission beamforming that sets delay times of the transducers of the ultrasound probe 2 with respect to the transmit signal, generating transmission drive signals for each of the transducers of the ultrasound probe 2. The transducers of the ultrasound probe 2 convert corresponding transmission drive signals to ultrasound, thereby emitting an ultrasound beam into the subject. Subsequently, the transducers of the ultrasound probe 2 acquire reflected ultrasound reflected from inside the subject, and convert the reflected ultrasound to transducer-received signals. The ultrasound signal acquirer 13 performs delay-and-sum on the transducer-received signals, and generates an acoustic line signal. The controller 11 acquires an acoustic line signal from the ultrasound signal acquirer 13 for each transmission event, and stores a plurality of acoustic line signals that make up one tomographic image as a tomographic image signal in the tomographic image storage 18.

Subsequently, a push pulse is transmitted (step S30). Specifically, the shear wave exciter 12 generates a pulsed ARFI signal by using a transmission profile held by the controller 11. Subsequently, the shear wave exciter 12 performs transmission beamforming that sets delay times of the transducers of the ultrasound probe 2 with respect to the ARFI signal, generating ARFI drive signals for each of the transducers of the ultrasound probe 2. Here, when a push pulse is first transmitted, an initial transmission profile is used that transmits a single push pulse of a predefined length, for example taking a center of an ROI as a focal point and using a predefined number of transducers including a center of a transducer array of the ultrasound probe 2. The transducers of the ultrasound probe 2 convert corresponding ARFI drive signals to ultrasound, thereby emitting a push pulse into the subject. When a transmission profile of transmission of two or more push pulses is used, each push pulse is transmitted consecutively.

Figure 3A:
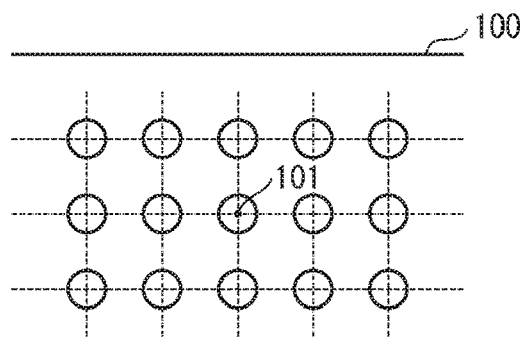
FIGS. 3A, 3B, 3C, 3D, 3E are schematic diagrams illustrating a time series of shear wave generation and displacement.
Figure 3B:
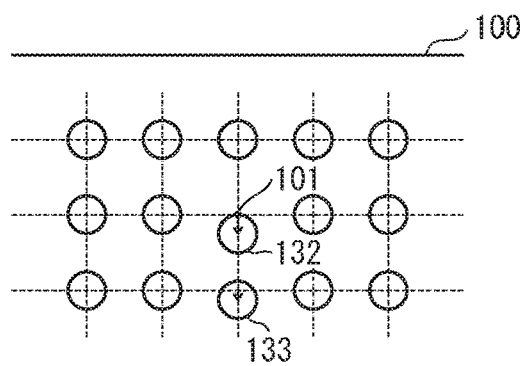
Figure 3C:
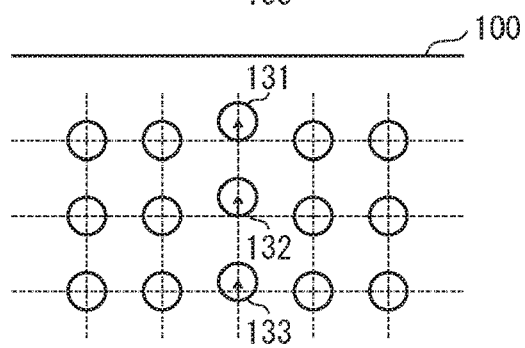
Figure 3D:
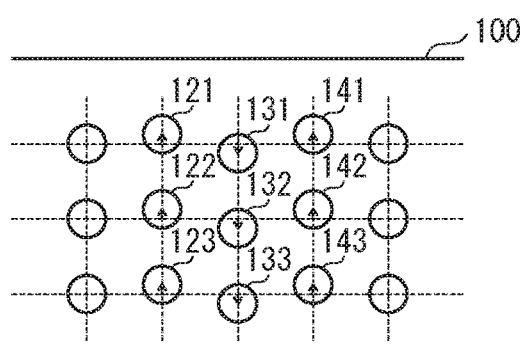
Figure 3E:
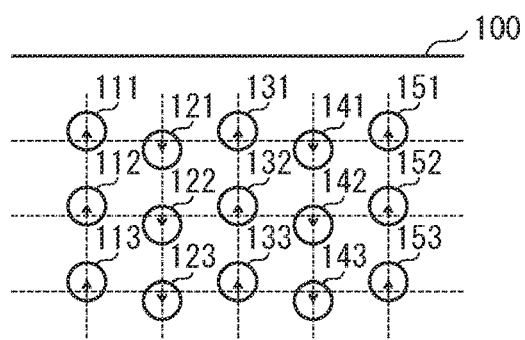

Here, generation of a shear wave by a push pulse is described with reference to FIGS. 3A, 3B, 3C, 3D, and 3E. FIG. 3A is a schematic diagram illustrating tissue of a subject in a region corresponding to an ROI, prior to push pulse application. In FIGS. 3A, 3B, 3C, 3D, and 3E, each "○" indicates a portion of tissue in an ROI in a subject, which is centered on an intersection of dashed lines when not under load. When the ultrasound probe 2 is in close contact with a skin surface 100 and applies a push pulse to a focal point 101, tissue 132 at the focal point 101 is pushed and shifted in the direction of the push pulse, as illustrated in the schematic diagram of FIG. 3B. Further, tissue 133 that is further in a travel direction of the push pulse than the tissue 132 is pushed by the tissue 132 and shifted in the travel direction of the push pulse. Subsequently, when push pulse transmission ends, the tissues 132, 133 attempt to return to their original positions, and therefore tissue 131, the tissue 132, and the tissue 133 start vibrating along the travel direction of the push pulse, as illustrated in FIG. 3C. As illustrated in the schematic diagram of FIG. 3D, vibrations propagate to tissues 121, 122, 123 and tissues 141, 142, 143, which are adjacent to the tissues 131, 132, 133. Further, as illustrated in the schematic diagram of FIG. 3E, vibrations further propagate to tissues 111, 112, 113 and tissues 151, 152, 153. Accordingly, in the subject, vibrations propagate in a direction perpendicular to the direction of vibration. In other words, a shear wave is generated at a point of application of the push pulse, and propagates in the subject.

Description continues with reference to FIG. 2. Subsequently, ultrasound is transmitted to and received from the ROI multiple times, and acquired ultrasound signals are stored (step S40). Specifically, immediately after push pulse transmission ends, an operation identical to that of step S20 is repeated, for example 10,000 times a second. Thus, during a period from immediately after generation of a shear wave until propagation ends, tomographic images of the subject are repeatedly acquired.

Subsequently, displacement of pixels is detected (step S50). Specifically, the displacement detector 14 acquires, as reference tomographic image signals, tomographic image signals stored in the tomographic image storage 18 in step S20.

As stated above, reference tomographic image signals are tomographic image signals acquired prior to push pulse transmission, i.e., prior to generation of a shear wave. Subsequently, the displacement detector 14 detects displacement of each pixel for each time of tomographic image signals from differences between the reference tomographic image signals and the tomographic image signals stored in the tomographic image storage 18. Specifically, a tomographic image signal is divided into regions of predefined size, for example eight by eight pixels, and displacement of pixels of the tomographic image signal is detected by pattern matching each region with the reference tomographic image signals. As a method of pattern matching, differences in brightness between corresponding pixels are detected, for example between each region and corresponding region of a same size in the reference tomographic image signals, and a sum of absolute values of the differences is calculated. The combination of region and reference region for which the sum is smallest is considered to be the same region and a distance between a reference point of the region (for example, a top left corner) and a reference point of the reference region is detected as a displacement. Size of a region may be a size other than eight pixels by eight pixels, and instead of a sum of absolute values of brightness difference a sum of squared brightness differences may be used. Further, as displacement, a difference in y coordinates (difference in depth) may be calculated between a reference point of a region and a reference point of a reference region. Thus, with respect to tissue of a subject corresponding to pixels of tomographic image signals, how far the tissue moves due to a push pulse or shear wave is calculated as displacement. Methods of calculating displacement are not limited to pattern matching. Any technique may be used for detecting movement amounts between two tomographic image signals, such as correlation processing between tomographic image signals and reference tomographic image signals. The displacement detector 14 generates a displacement image by associating displacement of each pixel in one tomographic image with coordinates, and outputs the displacement image to the displacement amount storage 19.

Subsequently, propagation analysis of shear waves is performed (step S60). Specifically, a wavefront of a shear wave is extracted from displacement images, generating wavefront images. From the wavefront images, wavefront position, amplitude, travel direction, and speed can easily be detected. Generation of a wavefront image is performed by, for example, extraction of a displacement region, thinning processing, spatial filtering, and time filtering, in this order.

Figure 4A:
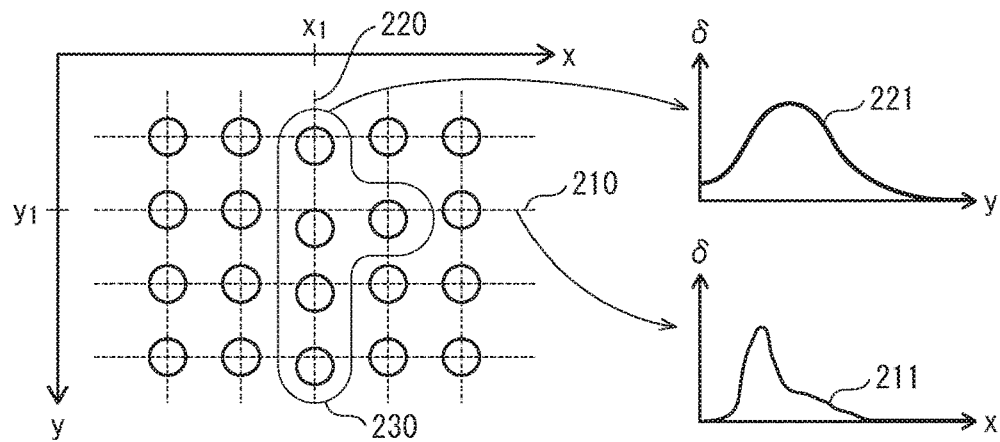
FIGS. 4A, 4B, 4C, 4D, 4E are schematic diagrams illustrating operation of shear wave propagation analysis pertaining to the embodiment.

Specific processing is described with reference to FIG. 4. FIG. 4A shows an example of a displacement image. As in FIG. 3A, each "○" in the drawing indicates a portion of tissue in a subject at an ROI, a position of which is centered on an intersection of dashed lines prior to application of a push pulse. The x axis is a direction in which transducers of the ultrasound probe 2 are arranged, and the y axis is a depth direction of the subject. The propagation analyzer 15 treats a displacement amount δ for each y coordinate as a function of coordinates x, and extracts a region for which a displacement amount δ is large, by using a dynamic threshold. Further, treating a displacement amount δ for each x coordinate as a function of coordinates y, and using a dynamic threshold, a region that exceeds a threshold is extracted as a region for which displacement amount δ is large. Here, a dynamic threshold is determined by performing signal analysis or image analysis of a target region. The threshold is not a fixed value, but varies according to factors such as width and maximum value of a signal of a target region. FIG.

4A illustrates a graph 211 in which displacement amount is plotted on a straight line 210 for which $y=y_1$, and a graph 221 in which displacement amount is plotted on a straight line 220 for which $x=x_1$. Thus, for example, a displacement region 230 in which a displacement amount δ is greater than the threshold can be extracted.

Figure 4B:
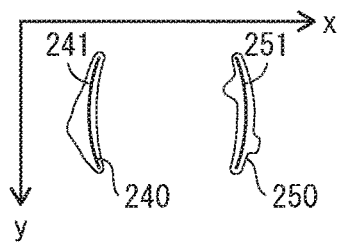
Figure 4C:
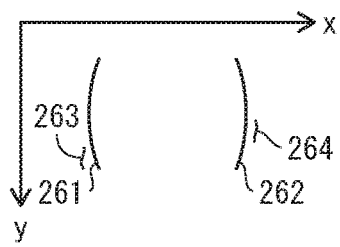
Figure 4D:
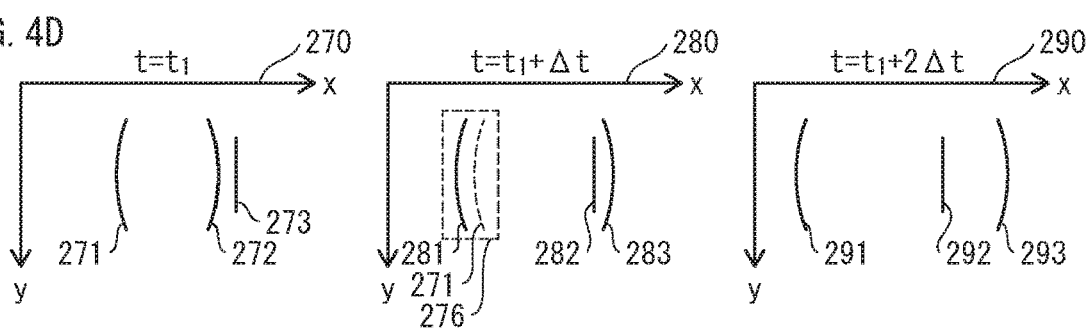
Figure 4E:
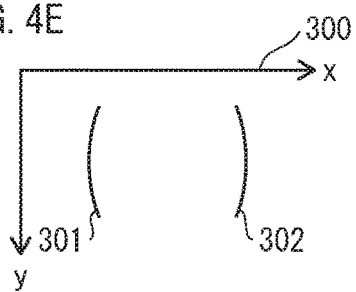

Subsequently, the propagation analyzer 15 extracts a wavefront by performing a thinning process on the displacement region. Displacement regions 240, 250 illustrated in the schematic diagram of FIG. 4B are each regions extracted as displacement regions. The propagation analyzer 15 extracts a wavefront by using, for example, the thinning algorithm of Hilditch. For example, in the schematic diagram of FIG. 4B, a wavefront 241 is extracted from the displacement region 240 and a wavefront 251 is extracted from the displacement region 250. Note that the thinning algorithm is not limited to Hilditch, and any thinning algorithm may be used. Further, for each displacement region, a process of removing coordinates for which a displacement amount δ is equal to or less than a threshold may be repeated while increasing the threshold until width of the displacement region is a single pixel.

Subsequently, the propagation analyzer 15 performs spatial filtering of wavefront image data that has undergone thinning processing, removing short wavefronts. For example, the propagation analyzer 15 detects the length of each wavefront extracted by thinning processing, and eliminates wavefronts that have a length less than half of the average length of all wavefronts extracted. Specifically, as indicated in the wavefront image of FIG. 4C, the propagation analyzer calculates the average length of wavefronts 261, 262, 263, 264, and eliminates as noise the wavefronts 263 and 264, which each have short lengths. Thus, erroneously detected wavefronts can be eliminated.

The propagation analyzer 15 performs the operations of displacement region extraction, thinning, and spatial filtering for all displacement images. Thus, wavefront image data is generated for displacement images in a one-to-one correspondence.

Finally, the propagation analyzer 15 performs time filtering on the wavefront image data to eliminate wavefronts that do not propagate. Specifically, in two or more wavefront images that are consecutive, changes in wavefront positions over time are detected, and a wavefronts that have an abnormal speed are eliminated as noise. The propagation analyzer 15, for example, detects changes in wavefront positions over time between a wavefront image 270 at time $t=t_1$, a wavefront image 280 at time $t=t_1+\Delta t$, and a wavefront image 290 at time $t=t_1+2\Delta t$. For example, with respect to wavefront 271, in wavefront image 280, the propagation analyzer 15 performs a correlation process in a region 276 that is centered on a position corresponding to the wavefront 271, the region 276 covering an area in which a shear wave could possibly move in the time period $\Delta t$ in directions perpendicular to the wavefront, i.e., the x axis direction in FIG. 4D. Thus, the correlation process is performed in a range that includes both a positive x axis direction (right in FIG. 4D) and a negative x axis direction (left in FIG. 4D) from the wavefront 271. This is to detect both transmitted and reflected waves. Thus, the propagation analyzer 15 detects that a movement destination of the wavefront 271 is a wavefront 281 in the wavefront image 280, and calculates a movement distance of the wavefront 271 over the time period $\Delta t$. In the same way, with respect to wavefronts 272 and 273, in the wavefront image 280, the propagation analyzer 15 performs a correlation process in regions that are centered on positions corresponding to each wavefront, covering areas in which a shear wave could possibly move in the time period $\Delta t$ in directions perpendicular to the wavefronts. Thus, the propagation analyzer 15 detects that the wavefront 272 moves to a position of a wavefront 283 and the wavefront 273 moves to a position of a wavefront 282. A similar process is performed between the wavefront image 280 and a wavefront image 290, detecting that the wavefront 281 moves to a position of a wavefront 291, the wavefront 282 moves to a position of a wavefront 292, and the wavefront 283 moves to a position of a wavefront 293. Here, the single wavefront indicated by the wavefront 273, the wavefront 282, and the wavefront 292 has a significantly shorter travel distance than other wavefronts, i.e. a significantly slower propagation speed. Such a wavefront is most likely a false positive, and is therefore eliminated as noise. Thus, as shown in a wavefront image 300 of FIG. 4E, wavefronts 301 and 302 are detected.

The propagation analyzer 15 outputs to the wavefront image storage 20 wavefront image data and correspondence information for each time. Here, correspondence information means information indicating which wavefront in each wavefront image a given wavefront corresponds to. For example, when it is detected that the wavefront 272 moves to the position of the wavefront 283, the correspondence information indicates that the wavefront 283 and the wavefront 272 are the same wavefront.

Figure 5A:
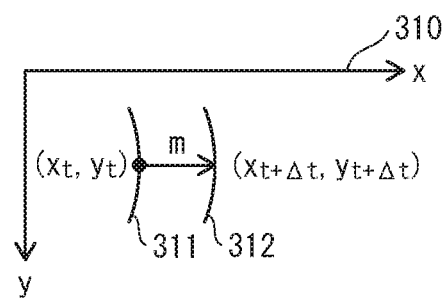
FIG. 5A is a schematic diagram illustrating elasticity measurement pertaining to the embodiment.
Figure 5B:
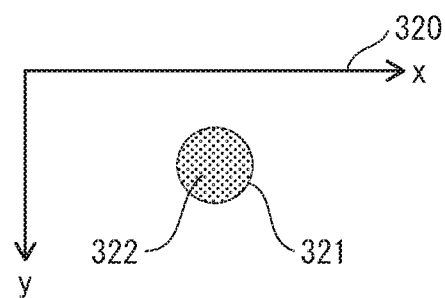
FIG. 5B is an example of an elasticity image pertaining to the embodiment.

Subsequently, elasticity images are generated and displayed (step S70). The propagation analyzer 15 generates elasticity images. Specifically, the propagation analyzer 15 detects wavefront position and speed for each time, from the wavefront image data and the correspondence information. Further, from the relationship between displacement images and tomographic images, for each pixel of each tomographic image, the propagation analyzer 15 calculates elastic modulus from the maximum speeds of shear waves in each displacement image, and generates elasticity images that associate the pixels and the elastic modulus of each tomographic image with each other. Generation of an elasticity image is described below using FIG. 5A and FIGS. 5B. FIG. 5A illustrates a wavefront image 310 derived by combining a wavefront image at a time t and a wavefront image at a time t+$\Delta$t. Here, it is assumed that correspondence information exists that indicates that a wavefront 311 at time t and a wavefront 312 at time t+$\Delta$t are the same wavefront. The propagation analyzer 15, from the correspondence information, detects coordinates $(x_{t+\Delta t}, y_{t+\Delta t})$ on the wavefront 312, which correspond with coordinates $(x_t, y_t)$ on the wavefront 311. Thus, the propagation analyzer 15 can estimate that a shear wave that passes through coordinates $(x_t, y_t)$ at time t arrives at coordinates $(x_{t+\Delta t}, y_{t+\Delta t})$ at time t+$\Delta$t. Accordingly, a velocity $v(x_t, y_t)$ of a shear wave that passes through coordinates $(x_t, y_t)$ can be estimated to be a value obtained by dividing a distance m between coordinates $(x_t, y_t)$ and coordinates $(x_{t+\Delta t}, y_{t+\Delta t})$ by a required time $\Delta t$. Thus, $v(x_t,y_t)=m/\Delta t=\sqrt{\{(x_{t+\Delta t}-x_t)^2+(y_{t+\Delta t}-y_t)^2\}}/\Delta t$. The propagation analyzer 15 performs the above process for all wavefronts, acquires shear wave speed at all coordinates each wavefront passes through, and calculates elastic modulus at each coordinate based on the shear wave speeds. The propagation analyzer 15, based on the elastic modulus at each coordinate, generates elasticity images on which color information is mapped. For example, as in FIG. 5B, an elasticity image 320 is generated in different colors in which coordinates for which the elastic modulus is equal to or greater than a certain value are red, coordinates for which the elastic modulus is less than the certain value are green, and coordinates for which elastic modulus could not be acquired are black. Classification need not be limited to two levels, and predefined stages of classification and color-coding may be performed. In FIG. 5B, region 322 is a region in which elastic modulus is equal to or greater than a certain value, corresponding to an inclusion 321. Note that although the inclusion 321 is clearly indicated in FIG. 5B, the inclusion 321 would not directly appear in an actual elasticity image. The propagation analyzer 15 outputs generated elasticity images to the controller 11, and the controller 11 outputs the elasticity images to the elasticity image storage 21. Further, the controller 11 performs a geometric transformation on elasticity images to transform them to image data for display, and outputs post-transformation elasticity images to the display 3.

Subsequently, propagation of shear waves is evaluated (step S80). The evaluator 16 acquires wavefront images from the wavefront image storage 20 via the controller 11 and evaluates how a shear wave propagates from wavefront position, amplitude, travel direction, and speed. The evaluator 16, for example, evaluates whether a shear wave propagates to an entire area of an ROI and whether a portion of propagation speed and/or direction of a shear wave is not uniform. As evaluation methods, for example, a propagation range diagram indicating shear wave propagation, a speed distribution diagram indicating speed distribution of a shear wave, etc., may be generated. The following describes specific examples of these with reference to FIG. 6A and FIG. 6B.

Figure 6A:
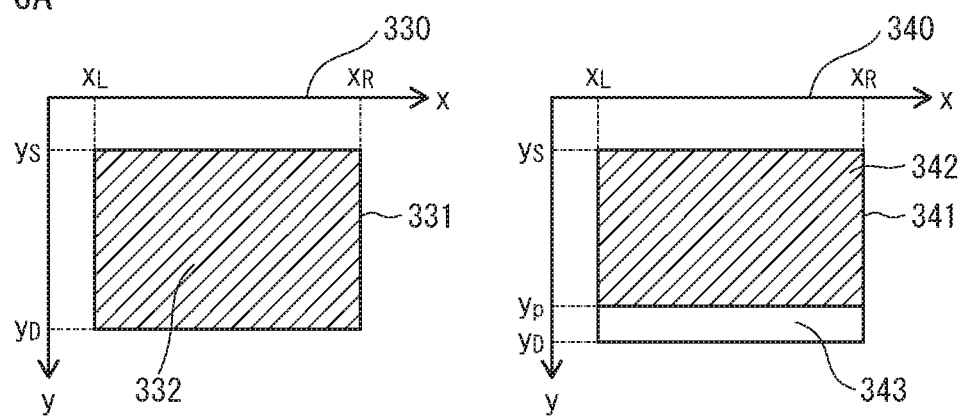
FIG. 6A is a schematic diagram illustrating an example of a propagation range diagram pertaining to the embodiment.
Figure 6B:
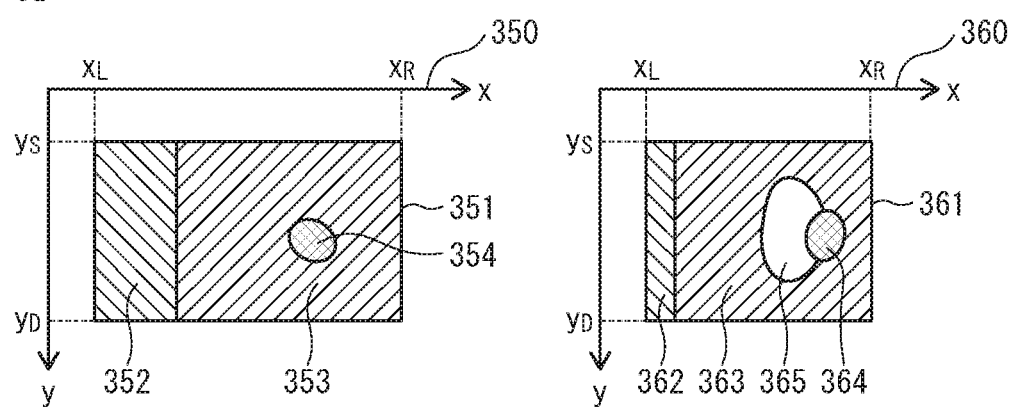
FIG. 6B is a schematic diagram illustrating an example of a shear wave speed distribution diagram pertaining to the embodiment.

FIG. 6A includes a propagation range diagram indicating shear wave propagation, in which a shear wave propagation region indicates a region through which a shear wave of a predefined amplitude or greater passes. In a propagation range diagram 330, an entire area of an ROI 331 ($x_L \leq x \leq x_R$, $y_S \leq y \leq y_D$) is a shear wave propagation region 332. On the other hand, in a propagation range diagram 340, in an ROI 341 ($x_L \leq x \leq x_R$, $y_S \leq y \leq y_D$), a region through which a shear wave of sufficient amplitude passes is a shear wave propagation region 342 ($y_S \leq y \leq y_p$), while a region through which a shear wave does not pass or through which a shear wave that did pass had insufficient amplitude is a non-propagation region 343 ($y_p \leq y \leq y_D$). Further, FIG. 6B includes a speed distribution diagram indicating shear wave speed distribution, in which shear wave propagation speed and direction is indicated by color. In a speed distribution diagram 350, a region 352 in which a shear wave propagates in a negative x axis direction (left) at a speed in a predefined range is green; and, among regions in which a shear wave propagates in a positive x axis direction (right), a region 353 in which speed of the shear wave is in a predefined range is blue, and a region 354 in which speed of the shear wave is faster than the predefined range is red. In a speed distribution diagram 360, a region in which a shear wave propagates left at a speed in a predefined range is green; and, among regions in which a shear wave propagates right, a region 363 in which speed of the shear wave is in a predefined range is blue, a region 364 in which speed of the shear wave is faster than the predefined range is red, and region 365 in which speed of the shear wave couldn't be acquired is black. Classification is not limited to these examples; for example, propagation speed may be evaluated as a scalar quantity and colored depending only on magnitude and not direction, and speed may be more finely graded.

Subsequently, whether or not it is necessary to adjust a push pulse transmission profile and re-measure is determined (step S90). Specifically, the controller 11 determines the necessity of re-measurement based on the evaluation results of the evaluator 16. For example, when a non-propagation region exists in a propagation range diagram, or when a region in which shear wave speed couldn't be acquired exists in a speed distribution diagram, the controller 11 determines that adjusting a push pulse transmission profile and re-measuring is necessary.

When determining that adjusting a push pulse transmission profile and re-measuring is not necessary, the controller 11 ends processing, displays an elasticity image, and accepts input from a user.

When the controller 11 determines that adjusting a push pulse transmission profile and re-measuring is necessary, adjustment of a transmission profile is performed (step S100). The push pulse adjuster 17 acquires from the controller 11 the push pulse transmission profile used in step S30 and content evaluated by the evaluator 16 in step S90. Subsequently, based on the content evaluated by the evaluator 16, the push pulse adjuster 17 optimizes the push pulse transmission profile. The following describes transmission profile optimization with reference to a flowchart and specific examples. FIG. 7 is a flowchart indicating push pulse transmission profile adjustment.

Initially, the push pulse adjuster 17 determines whether a non-propagation region exists in the ROI, in which no shear waves propagate (step S110). When a non-propagation region exists in the ROI, the push pulse adjuster 17 determines the shape of the non-propagation region. Specifically, the push pulse adjuster 17 determines whether the non-propagation region extends in the transducer array direction (a region in which y coordinates are in a specific range and x coordinates are not), or whether the non-propagation region extends in the depth direction (a region in which x coordinates are in a specific range and y coordinates are not) (step S111). Here, when a non-propagation region is surrounded by a shear wave propagation region (a region in which x coordinates are in a specific range and y coordinates are in a specific range), it is considered to extend in the depth direction; the reasoning for this is provided later.

Figure 8A:
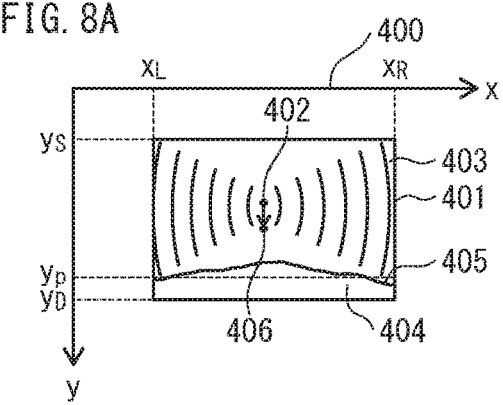
FIG. 8A is a schematic diagram illustrating an example of a shear wave non-propagation region and transmission profile adjustment.
Figure 8B:
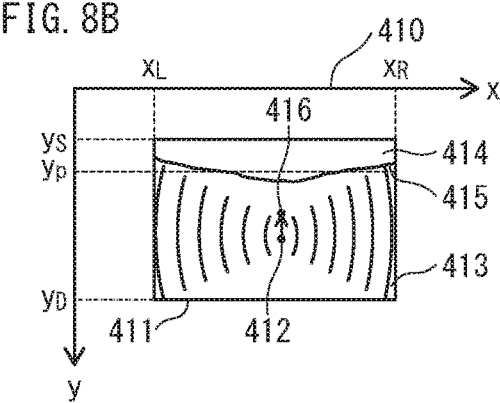
FIG. 8B is a schematic diagram illustrating an example of a shear wave non-propagation region and transmission profile adjustment.

When a non-propagation region extends in the array direction, the position of the non-propagation region in the depth direction is determined (step S112). When a non-propagation region is at a shallow end of the ROI or at a deep end of the ROI, i.e., when all of a region shallower than a certain depth in the ROI or all of a region deeper than a certain depth in the ROI is a non-propagation region, the push pulse adjuster 17 adjusts depth (y coordinates) of the focal point of a push pulse to be closer to the non-propagation region (step S113). More specifically, when a region equal to or greater than a certain depth is a non-propagation region, the focal point of a push pulse is made deeper, and when a region equal to or less than a certain depth is a non-propagation region, the focal point of a push pulse is made shallower. As a propagation range diagram 400 in FIG. 8A illustrates, a focal point 402 of a push pulse is too shallow with respect to an ROI 401, and therefore a non-propagation region 404 is generated in the ROI 401. Further, as a propagation range diagram 410 in FIG. 8B illustrates, a focal point 412 of a push pulse is too deep with respect to an ROI 411, and therefore a non-propagation region 414 is generated in the ROI 411. In the propagation range diagram 400 and the propagation range diagram 410, wavefronts are illustrated to aid description. With respect to the propagation range diagram 400 of FIG. 8A, by using an average value $y_p$ of y coordinates at a boundary line 405 between a shear wave propagation region 403 and the non-propagation region 404, a focal point 406 of a new push pulse, for example, is moved $(y_D - y_p)/2$ in a positive direction of the y axis (direction of increasing depth) from the focal point 402 of the previous push pulse. Similarly, with respect to the propagation range diagram 410 of FIG. 8B, by using an average value $y_p$ of y coordinates at a boundary line 415 between a shear wave propagation region 413 and the non-propagation region 414, a focal point 416 of a new push pulse, for example, is moved $(y_p-y_S)/2$ in a negative direction of the y axis (direction of decreasing depth) from the focal point 412 of the previous push pulse. In other words, a focal point of a push pulse is moved towards a non-propagation region by half the average range of the non-propagation region in the depth direction (y direction) of the ROI. Thus, a "depth" parameter of a transmission profile is changed. As the y coordinate $y_p$ of a boundary between a shear wave propagation region and a non-propagation region, a maximum value of a boundary line between a shear wave propagation region and a non-propagation region may be used when the non-propagation region is deeper than the shear wave propagation region, and a minimum value of a boundary line between a shear wave propagation region and a non-propagation region may be used when the non-propagation region is shallower than the shear wave propagation region. Further, a distance a y coordinate of a focal point of a push pulse is moved may be $(y_D-y_p)/4$ or $(y_D-y_p)$, but $(y_D-y_p)/2$ is most likely to make another adjustment of focal point of a push pulse unnecessary, and is therefore preferred.

Figure 8C:
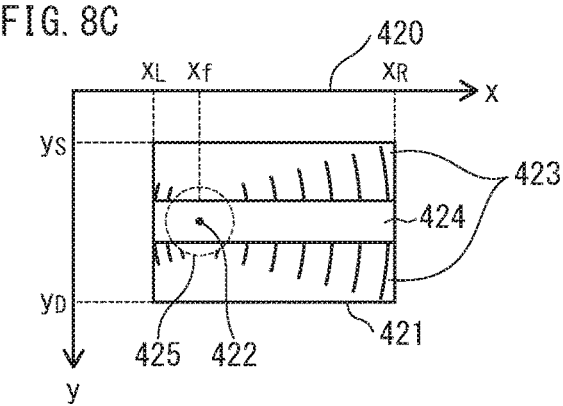
FIG. 8C is a schematic diagram illustrating an example of a shear wave non-propagation region.
Figure 8D:
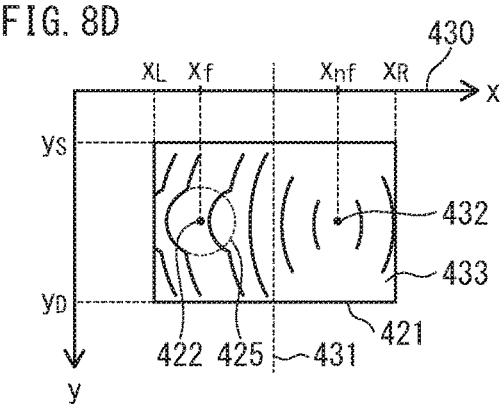
FIG. 8D is a schematic diagram illustrating an example of transmission profile adjustment with respect to the propagation range diagram of FIG. 8C.

When a non-propagation region extends in the transducer array direction and the non-propagation region is sandwiched between shear wave propagation regions (when shear wave propagation regions are present at both deeper and shallower sides of the non-propagation region), a focal point of a push pulse is moved along the transducer array direction (x direction) (step S114). As a propagation range diagram 420 of FIG. 8C illustrates, when a focal point 422 of a push pulse is in a hard region 425, insufficient tissue movement is generated by the push pulse and a non-propagation region 424 is assumed to be generated between shear wave propagation regions 423 in an ROI 421. In this case, by moving a focal point of a push pulse in the transducer array direction (x direction), the new focal point is set to be outside the hard region 425. For example, as a propagation range diagram 430 illustrates, a straight line 431 that is parallel to the depth direction (y axis direction) is assumed to pass through a center of the ROI 421, and a focal point 432 of a new push pulse is set to mirror the focal point 422 of the previous push pulse across the straight line 431. More specifically, a range of x coordinates of the ROI 421 is $x_L \leq x \leq x_R$, and when an x coordinate of the focal point 422 is $x_f$, an x coordinate of the focal point 432 is $x_{nf}=x_L+x_R-x_f$. By changing "depth" and "direction and angle of propagation of a push pulse relative to the ultrasound probe" of the transmission profile, x coordinates of a focal point are changed. Thus, by setting a focal point of a push pulse outside the hard region 425, a shear wave propagation region 433 can be expected to extend across an entirety of the ROI 421. The x coordinate of a focal point of a new push pulse is not limited to being set to $x_{nf}$. For example, the x coordinate may be shifted a predefined amount from $x_f$ towards a center of the ROI 421 (for example, a quarter of the range in the x direction of the ROI 421).

When a non-propagation region extends in a depth direction, including a case in which the non-propagation region is surrounded by a shear wave propagation region, a point of the non-propagation region in the transducer array direction is determined (step S115). Note that when a non-propagation region is surrounded by a shear wave propagation region, the non-propagation region is considered to be sandwiched by shear wave propagation regions.

When a non-propagation region extends in the depth direction and is at one end of the ROI in the transducer array direction, i.e., the non-propagation region covers all values of x greater or less than a given x coordinate in the ROI, a push pulse is adjusted to be stronger (step S116). As illustrated in a propagation range diagram 440 of FIG. 8E, a shear wave propagated from a focal point 442 of a push pulse attenuates at an end of a shear wave propagation region 443 and does not propagate to an entirety of an ROI 441, generating a non-propagation region 444. More specifically, any of the following adjustments are performed:

(1) at least one of the following variables are increased: a number of transducers used in outputting a push pulse; a transmission time of a push pulse; and a voltage of an ARFI drive signal applied to transducers, thereby increasing amplitude of a shear wave caused by a push pulse. More specifically, for example, a number of transducers used in transmitting a push pulse may be increased by four, transmission time of a push pulse may be increased by 20 μs, and a voltage of an ARFI drive signal may be increased by 10%. Two or more of the above may be performed simultaneously.

(2) The number of push pulses consecutively transmitted is increased and a focal point of a new push pulse is set to be in the non-propagation region or in the vicinity of the non-propagation region, thereby causing a shear wave to propagate to the non-propagation region. More specifically, for example, as illustrated in a propagation range diagram 450 of FIG. 8F, a straight line 451 that is parallel to the depth direction (y axis direction) is assumed to pass through a center of the ROI 441, and a focal point 452 of a second push pulse is set to mirror the focal point 442 of the previous push pulse across the straight line 451.

As an adjustment, increasing the number of push pulses consecutively transmitted is most preferable, and then increasing the number of transducers used in transmission of a push pulse, lengthening transmission time of a push pulse, and increasing voltage of an ARFI drive signal are listed here in order of preference, for the reasons described below. When considering effects on a subject, minimal displacement of tissue in the subject is preferable, and in particular a low maximum value of tissue displacement is preferable. However, in order to improve hardness measurement accuracy, the average value and minimum value of displacement is preferably high. Accordingly, taking both into account, a small difference between the maximum value and the average value of displacement is preferable, and therefore rather than a low number of strong push pulses, a large number of not-too-strong push pulses is preferable. Further, when transmitting a strong push pulse, increasing sound pressure of ultrasound is not as preferable as increasing transmission duration of ultrasound, which in turn is not as preferable as improving an area of passage and focus of ultrasound, in order to limit the impact of a push pulse passing through tissue other than at the focal point thereof.

When a non-propagation region extends in the depth direction and is sandwiched between shear wave propagation regions or surrounded by a shear wave propagation region, adjustment is made to output two push pulses to different focal points (step S117). In this step, the push pulse adjuster 17 sets focal points for two push pulses in the shear wave propagation regions that sandwich the non-propagation region in the transducer array direction. In this case, it is likely that inside the non-propagation region is a reflector of shear waves, for example, hard tissue. Thus, the following two possibilities may be considered: (i) as illustrated in a propagation range diagram 460 in FIG. 8G, shear waves in a non-propagation region 464 cannot be correctly detected due to interference between a shear wave propagating from a focal point 462 of a push pulse and a reflected shear wave spreading from a reflector 465 in an ROI 461, or (ii) when a reflector is much harder than surrounding tissue, the reflector greatly reflects shear waves and shear waves hardly propagate through the reflector at all (in this case the region in which the reflector is present is the non-propagation region). In either case, in order to make shear waves propagate to the non-propagation region, it is preferable to set focal points of push pulses to multiple locations in the vicinity of the non-propagation region to set focal points of two push pulses in the shear wave propagation region either side of the non-propagation region in the transducer array direction. For example, with respect to the propagation range diagram 460 of FIG. 8G, one focal point is set in a shear wave propagation region 463 and one focal point is set in a shear wave propagation region 466. For example, a focal point 467 of a new push pulse is added in the shear wave propagation region 466. In this case, the focal point 462 may continue to be used as a focal point of a push pulse in the shear wave propagation region 463.

When a non-propagation region is not present in an ROI, a focal point of a push pulse is set in the vicinity of a region in which propagation speed of a shear increases locally and/or in a region in which shear wave speed is uniform (step S118). In this case, the number of push pulse transmissions is increased by one, and in addition to the focal point of the push pulse in step S30, a push pulse is also transmitted to a newly set focal point. For example, in a speed distribution diagram 470 in FIG. 8H, with respect to an ROI 471, shear waves propagate in the x direction (left direction) from a focal point 476 of a push pulse, and although shear wave propagation speed is uniform in a region 472 and a region 473, shear wave propagation speed increases locally in a region 474 and shear wave propagation speed is not acquired in a region 475. In this case, in addition to the focal point 476, a focal point 477 of a push pulse is added to the region 473, in which shear wave propagation speed is uniform, in the vicinity of the region 474, in which shear wave propagation speed is high. In this case, the focal point 477 preferably satisfies the following two conditions. The first condition is that the focal point is in the vicinity of a region in which shear wave propagation speed changes. This is because setting a focal point of a push pulse that causes shear wave vibrations near tissue of different hardness to surrounding tissue, which corresponds to a region in which shear wave propagation speed changes, causes propagation of shear waves of large amplitude into the tissue, allowing accurate acquisition of hardness of the tissue. The second condition is that the focal point is in a region of uniform shear wave propagation speed. This is to try and avoid refraction and reflection of shear waves by regions other the targeted region in which shear wave propagation speed changes, and increase reliability of shear wave propagation speed measurement. Note that only one of the above conditions being satisfied is also possible. When two or more focal points of push pulses become close to each other as a result of adding a focal point, it is possible to not transmit a push pulse to a prior focal point that is close to a newly set focal point.

Description continues with reference to FIG. 2. When the controller 11 receives a push pulse transmission profile after adjustment from the push pulse adjuster 17, steps S30 to S90 are executed using the push pulse transmission profile after adjustment, in order to transmit a push pulse and generate an elasticity image.

<Summary>

According to the above configuration, a push pulse transmission profile can be optimized based on shear wave propagation. Thus, an operator does not have to engage in trial and error based on an elasticity image, and tissue hardness of a subject in an ROI can be accurately measured. Further, according to the above configuration, after optimization of a push pulse transmission profile, tissue hardness measurement can be performed. Thus, an operator has only to apply the ultrasound probe to the subject until an elasticity image is acquired.

<<Modification 1>>

According to the embodiment, when shear waves do not propagate across an entirety of an ROI, a push pulse transmission profile is adjusted based on position and shape of a non-propagation region.

However, independently of whether or not shear waves propagate across an entirety of an ROI, adjustment of a push pulse transmission profile may be performed taking into consideration, for example, shear wave propagation speed.

<Transmission Profile Adjustment>

Figure 8E:
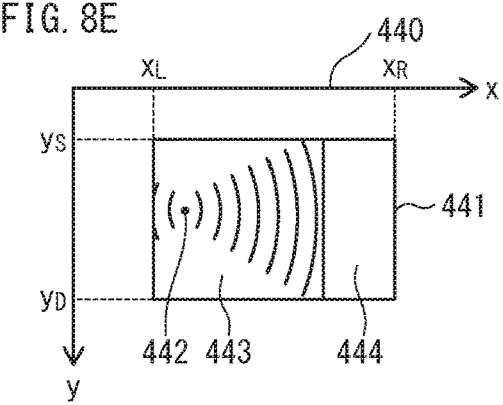
FIG. 8E is a schematic diagram illustrating an example of a shear wave non-propagation region.
Figure 8F:
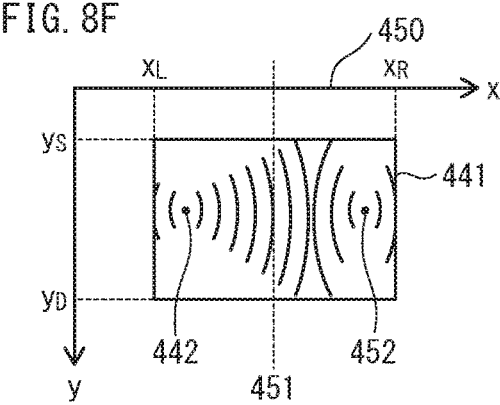
FIG. 8F is a schematic diagram illustrating an example of transmission profile adjustment with respect to the propagation range diagram of FIG. 8E.
Figure 8G:
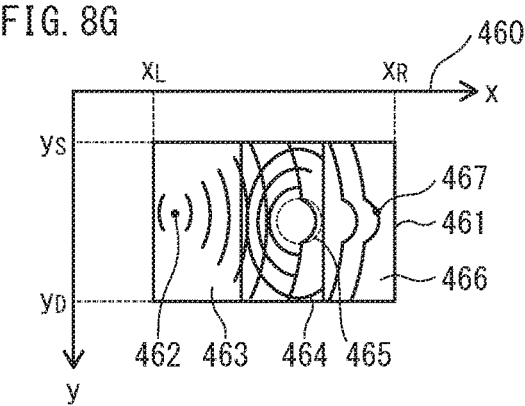
FIG. 8G is a schematic diagram illustrating an example of a shear wave non-propagation region and transmission profile adjustment.
Figure 8H:
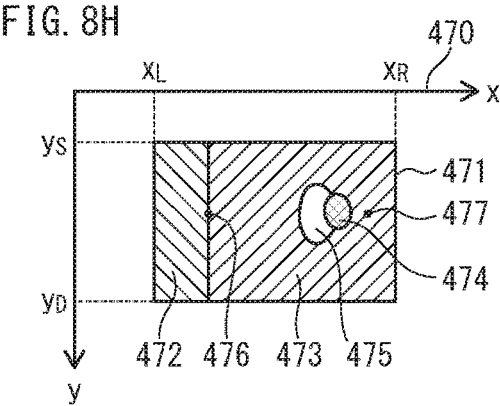
FIG. 8H is a schematic diagram illustrating an example of shear wave speed distribution and transmission profile adjustment.
Figure 9A:
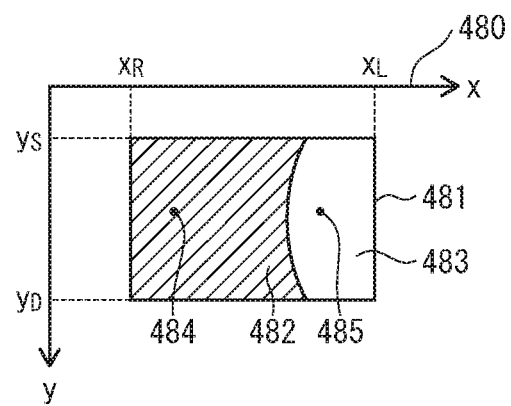
FIG. 9A is a schematic diagram illustrating an example of a shear wave non propagation region and transmission profile adjustment pertaining to Modification 1.
Figure 9B:
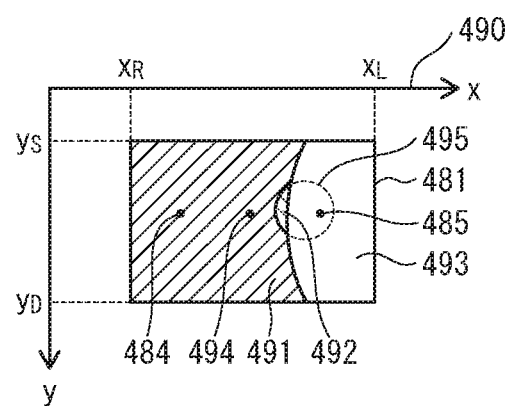
FIG. 9B is a schematic diagram illustrating an example of shear wave speed distribution and transmission profile adjustment corresponding to FIG. 9A.

A specific example is illustrated in FIG. 9A and FIG. 9B. FIG. 9A, similarly to FIG. 8E, shows a propagation range diagram 480 in which a non-propagation region 483 extends in the depth direction at one end of an ROI 481 in the transducer array direction. A focal point of a push pulse is denoted by 484, and a region 482 is a shear wave propagation region. FIG. 9B is a shear wave speed distribution diagram 490 corresponding to the propagation range diagram 480 of FIG. 9A. In the ROI 481, a region 493 that corresponds to the non-propagation region 483 is a region in which shear wave speed could not be acquired. However, in a region corresponding to the shear wave propagation region 482 is a region 491 in which shear wave speed is uniform and a region 492 in which shear wave speed is locally high. In such a case, as a location for a newly-added focal point of a push pulse, rather than a focal point 485 that mirrors the focal point 484 across a straight line parallel to the depth direction (y axis direction) that passes through a center of the ROI 481, a focal point 494 is preferred that (a) is in the region 491 in which shear wave speed is uniform and (b) is in the vicinity of the region 492 in which shear wave speed is locally high. This is because the existence of hard tissue 495 that includes the region 492 can be assumed from the presence of the region 492, in which shear wave propagation speed is locally high, and a region that the hard tissue 495 occupies is not clear from the non-propagation region 483, i.e., the region 493 in which shear wave speed could not be acquired. Accordingly, if the focal point 485 is set in the non-propagation region 483, there is a risk of the focal point 485 being set in the hard tissue 495. In this case, it is preferable that the focal point 494 be set in the shear wave propagation region 482 in the vicinity of the non-propagation region 483, that the focal point 494 be set in the region 491 in which shear wave speed is uniform, and that the focal point 494 be set in the vicinity of the region 492 in which shear wave speed is locally high.

Without being limited to this case, controlling a focal point of a push pulse may be performed taking into consideration shear wave propagation speed distribution when changing or adding a focal point, setting the focal point in the vicinity of a local change in shear wave propagation speed and/or in a region in which shear wave propagation speed is uniform.

<Summary>

According to Modification 1, when changing or adding a focal point of a push pulse, not only whether shear wave propagation covers an entirety of an ROI, but also by aiming to increase measurement accuracy in regions of different hardness and/or aiming to reliability of shear wave propagation speed measurement, the likelihood of having to re-measure after adjustment is reduced, the number of times tissue hardness is measured is reduced, the duration of measurement is reduced, and burden on the subject is reduced.

<<Modification 2>>

In the Embodiment and Modification 1, whether or not shear wave propagation covers an entirety of an ROI, and shear wave propagation speed distribution, are determined by using wavefronts of shear waves.

According to Modification 2, presence of shear wave propagation and/or speed distribution can be determined by a simple method.

<Analysis of Presence of Shear Wave Propagation>

According to this modification, when generating a propagation range diagram, whether or not a shear wave has passed through points in an ROI is not generated from a wavefront image, but instead from a displacement image. In other words, at any time, a location in which displacement is detected is considered be a location through which a wavefront has passed. More specifically, with respect to points in an ROI, a maximum absolute value of displacement at the same point over a plurality of displacement images is detected, and when the maximum value is equal to or greater than a predefined threshold, the point is considered to be a point through which a shear wave has passed. When the maximum value is less than the predefined threshold, the point is considered to be a point through which a shear wave has not passed.

Accordingly, if there is a region for which displacement could not be detected at any time, the region is considered a non-propagation region and a push pulse transmission profile is adjusted to make a shear wave propagate to the non-propagation region.

<Analysis of Shear Wave Propagation Speed>

According to this modification, in analysis of shear wave speed, a speed distribution diagram indicating speed at which shear waves passed through points of an ROI is not generated and instead tomographic images themselves are used. In a tomographic image, a region in which brightness is locally low is considered to be a region in which shear wave speed is locally different. This is because brightness of a region of different hardness, such as that of a tumor, is often low in comparison to a surrounding area, and therefore the likelihood of the region being tissue of a different hardness, such as a tumor, is high.

Accordingly, when a focal point of a push pulse is changed or added, the focal point is set to a location that is not in a region of a tomographic image in which brightness is locally low and/or is set to be in the vicinity of a region of the tomographic image in which brightness is locally low.

<Summary>

According to this configuration, evaluation can be performed without detecting wavefronts. Thus, the wavefront image storage is not required. Further, when generating an elasticity image, a method directly based on a displacement image and not based on a wavefront image is used, and therefore the invention can be implemented without requiring detection of wavefronts and without the propagation analyzer. As a method of generating an elasticity image directly based on a displacement image, a conventional method may be used in which, for each pixel in the displacement image, a time at which displacement is first detected is considered to be the time at which a shear wave passes through.

Further, by predicting presence or absence of a tumor region by using brightness of a tomographic image, adjustment of a push pulse transmission profile can be performed even when wavefront speed or elasticity is unclear. Thus, it is possible to adjust a push pulse transmission profile without calculating wavefront speed or measuring elasticity, and to adjust a push pulse transmission profile based on a tomographic image.

Further, according to this modification, when it is determined that a simple evaluation would make a re-measurement necessary, instead of adjusting a push pulse transmission profile directly based on the simple evaluation, wavefronts may be detected, evaluation performed based on the wavefronts, and the push pulse transmission profile adjusted based thereon.

<<Modification 3>>

According to the Embodiment and Modifications 1 and 2, the shear wave propagation analysis in step S60 is performed according to extraction of displacement regions, thinning processing, spatial filtering, and time filtering, in that order.

According to Modification 3, shear wave propagation analysis features detection of peak time of displacement at each location, time filtering, and spatial filtering, performed in that order.

Because this modification is the same as the Embodiment aside from the shear wave propagation analysis in step S60, the following only describes the differences in shear wave propagation analysis.

<Shear Wave Propagation Analysis>

Figure 10A:
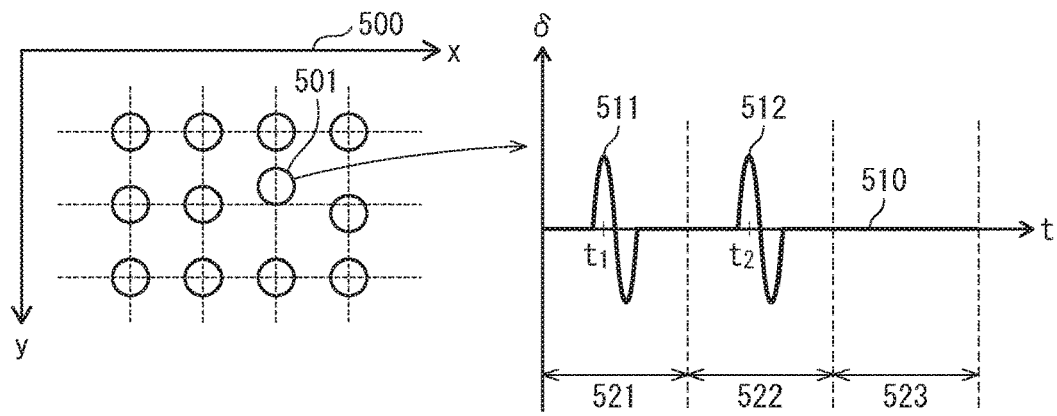
FIGS. 10A, 10B, 10C, 10D, 10E are schematic diagrams illustrating operation of shear wave propagation analysis pertaining to Modification 3.
Figure 10B:
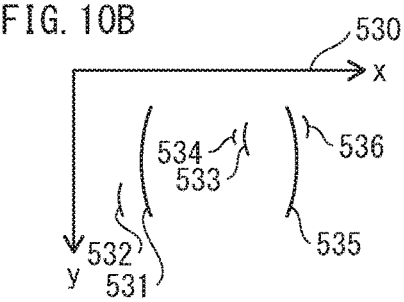
Figure 10C:
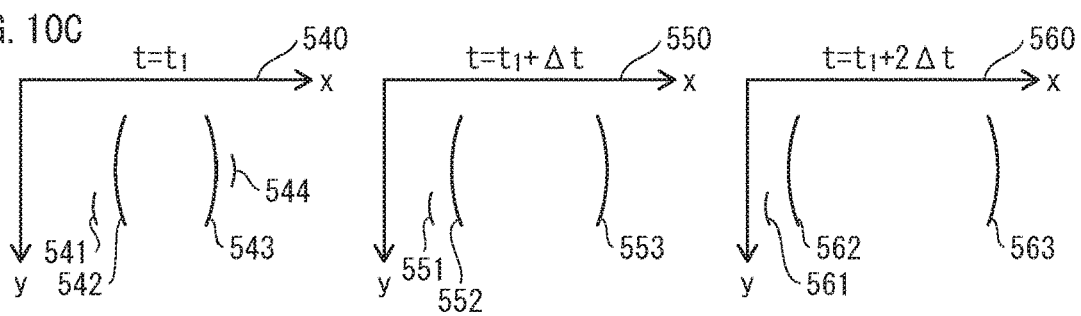
Figure 10D:
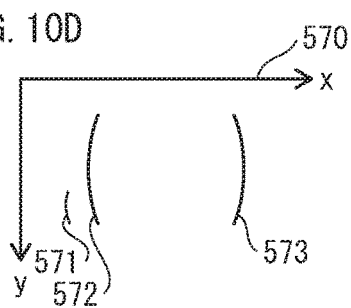

Initially, for each pixel, correlation processing is performed for displacement at each time and region, and displacement peaks are detected. A propagation analyzer acquires a displacement image from the displacement amount storage 19. The following description references FIGS. 10A, 10B, 10C, 10D, and 10E. FIG. 10A shows an example of a displacement image. As in FIGS. 3A and 4A, each "○" in the drawing indicates a portion of tissue in a subject at an ROI, a position of which is centered on an intersection of dashed lines prior to application of a push pulse. The x axis is a direction in which transducers of the ultrasound probe 2 are arranged, and the y axis is a depth direction of the subject. The propagation analyzer detects a time of an extreme value of displacement δ for each coordinate. Here, an extreme value means a maximum value or a minimum value, i.e., the greatest absolute value when the displacement δ is negative. In the present modification, only times when the displacement δ is a maximum value, i.e., positive, are detected. A graph 510 in FIG. 10A shows the displacement δ at a point 501, at coordinates $(x_1, y_1)$, as a function of time t. Here, the displacement δ is treated as a one-dimensional vector, and therefore the displacement δ is a value indicating only displacement in the y-axis direction. Further, displacement in the direction of depth (y coordinates increase) is positive and displacement in the opposite direction (y coordinates decrease) is negative. The propagation analyzer, for example, divides time in which tomographic image signals are acquired into sections 521, 522, 523. The propagation analyzer performs correlation processing for the displacement δ in section 521, the displacement δ in section 522, and the displacement δ in section 523, and thereby detects times $t_1$, $t_2$ at which the displacement δ peaks. Here, the reason for the division of the time in which tomographic image signals are acquired into sections is that due to the passage of reflected waves through a point of interest, for example, wavefronts may pass through a point of interest multiple times. In the present modification, only the time at which the displacement δ is a maximum is detected. However, in correlation processing, a time at which a correlation value is negative, i.e., a maximum absolute value, may be detected. In this way, a wavefront of inverted phase can be further detected.

Subsequently, the propagation analyzer extracts a set of pixels in which displacement is large as a wavefront. More specifically, the propagation analyzer, for each time, acquires a set of points at which the displacement δ peaks as a displacement region, and extracts each displacement region as a wavefront. For example, as shown in a wavefront image 530 in FIG. 10B, at time $t_1$, a displacement region 531 that includes a point at coordinates $(x_1, y_1)$ and displacement regions 532, 533, 534, 535, 536 are each extracted as wavefronts. As noted above, based on sets of pixels for which negative values of displacement δ are maximum absolute values, phase-inverted wavefronts may be extracted as detected wavefronts. The propagation analyzer stores extracted wavefronts as wavefront image data.

Subsequently, the propagation analyzer performs time filtering on the wavefront image data to eliminate wavefronts that do not propagate. Specifically, as in the time filtering of step S60, in two or more wavefront images that are temporally consecutive, changes in wavefront positions over time are detected, and a wavefronts that have an abnormal speed are eliminated as noise. The propagation analyzer, for example, detects changes in wavefront position over time between a wavefront image 540 at time $t=t_1$ and a wavefront image 550 at time $t=t_1+\Delta t$, and between the wavefront image 550 at time $t=t_1+\Delta t$ and a wavefront image 560 at time $t=t_1\ 2\Delta t$. Detection of changes in wavefront position over time is performed by correlation processing, as in the time filtering of step S60. For example, with respect to the wavefronts in the wavefront image 540, the propagation analyzer performs correlation processing in regions of the wavefront image 550 that are centered on positions corresponding to each wavefront in the wavefront image 540, covering areas in which a shear wave could possibly move in the time period Δt in directions perpendicular to the wavefronts. For example, between the wavefront image 540 and the wavefront image 550, a wavefront 541 is detected as having moved to the position of a wavefront 551, a wavefront 542 is detected as having moved to the position of a wavefront 552 and a wavefront 543 is detected as having moved to the position of a wavefront 553. Here, a destination of a wavefront 544 is not detected, for the following reason. In correlation processing of a wavefront image X including a wavefront A and a wavefront B, when a region centered on the wavefront A and a region centered on the wavefront B overlap, and a wavefront C is present in the overlap, destinations are determined in the following way. Correlation between the wavefront A and the wavefront C, and correlation between the wavefront B and the wavefront C are calculated, and (1) if only one correlation exceeds a threshold value, the correlation that exceeds the threshold value is determined to be the origin of the wavefront C, (2) if both correlations exceed the threshold value, the higher correlation with the wavefront C is determined to be the origin of the wavefront C, and (3) if both correlations are equal to or below the threshold value, no origin of the wavefront C is determined. Because the wavefronts 542, 543, 552, and 553 are approximately the same length as each other and the wavefront 544 is significantly shorter, the correlation between the wavefront 543 and the wavefront 553 is higher than the correlation between the wavefront 544 and the wavefront 553. Thus, in the region of the wavefront image 550 centered on the same position as the wavefront 544, no wavefront is present as a destination of the wavefront 544. The wavefront 544 that has no destination is eliminated as noise. In the same way, between the wavefront image 550 and the wavefront image 560, a wavefront 551 is detected as having moved to the position of a wavefront 561, a wavefront 552 is detected as having moved to the position of a wavefront 562 and a wavefront 553 is detected as having moved to the position of a wavefront 563. The propagation analyzer stores the wavefront image data after the time filtering. The propagation analyzer may further store correspondence information as described in the embodiment.

Figure 10E:
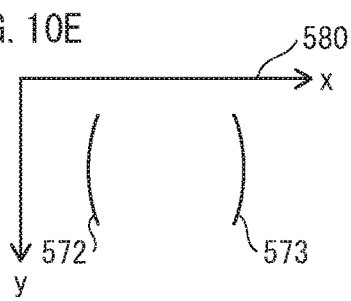

Subsequently, the propagation analyzer performs spatial filtering of wavefront image data that has undergone time filtering, removing short wavefronts. More specifically, as in the spatial filtering in step S60, length of each wavefront in each wavefront image is detected, and wavefronts shorter than a predefined length, for example wavefronts shorter than half the average length of all wavefronts, are eliminated as noise. Specifically, as indicated in the wavefront image 570 of FIG. 10D, the propagation analyzer calculates the average length of wavefronts 571, 572, and 573, and eliminates as noise the wavefront 571, which has a short length. Thus, erroneously detected wavefronts can be eliminated. The propagation analyzer may, from wavefront correspondence information, eliminate other wavefronts in the wavefront images that share the same location as an eliminated wavefront. As illustrated in FIG. 10E, only the wavefronts 572 and 473 remain in the wavefront image 480 after spatial filtering.

The propagation analyzer outputs to the wavefront image storage 20 wavefront image data after spatial filtering and correspondence information, via the controller.

<Summary>

In this modification, propagation analysis based on displacement changes over time for each position in tissue is described. Because peak displacement in a time series for each coordinate is detected, displacement that does not change over time is not detected, and therefore noise that does not change over time, such as noise in reference tomographic image signals and position shift between a reference tomographic image signal and tomographic image signals, is not erroneously detected as displacement. Further, because peak displacement in a time series for each coordinate is detected multiple times, if a wavefront passes through one location multiple times, and in particular if transmitted waves and reflected waves pass through, wavefronts can be extracted. Further, when detecting peak displacement in a time series for each coordinate, by detecting times at which correlation is negative and an absolute value is a maximum, cases in which phase of a shear wave is inverted can be detected, and even in cases in which a shear wave is reflected such as fixed end reflection, reflected wavefronts can be detected.

<<Modification 4>>

According to the embodiment and modifications 1 to 3, in step S70, a generated elasticity image is outputted to the display 3.

According to Modification 4, until a push pulse transmission profile is determined, a user is notified by outputting a notification screen indicating that measurement of hardness of a subject by the ultrasound diagnostic device is complete or incomplete.

<Operations>

Figure 11:
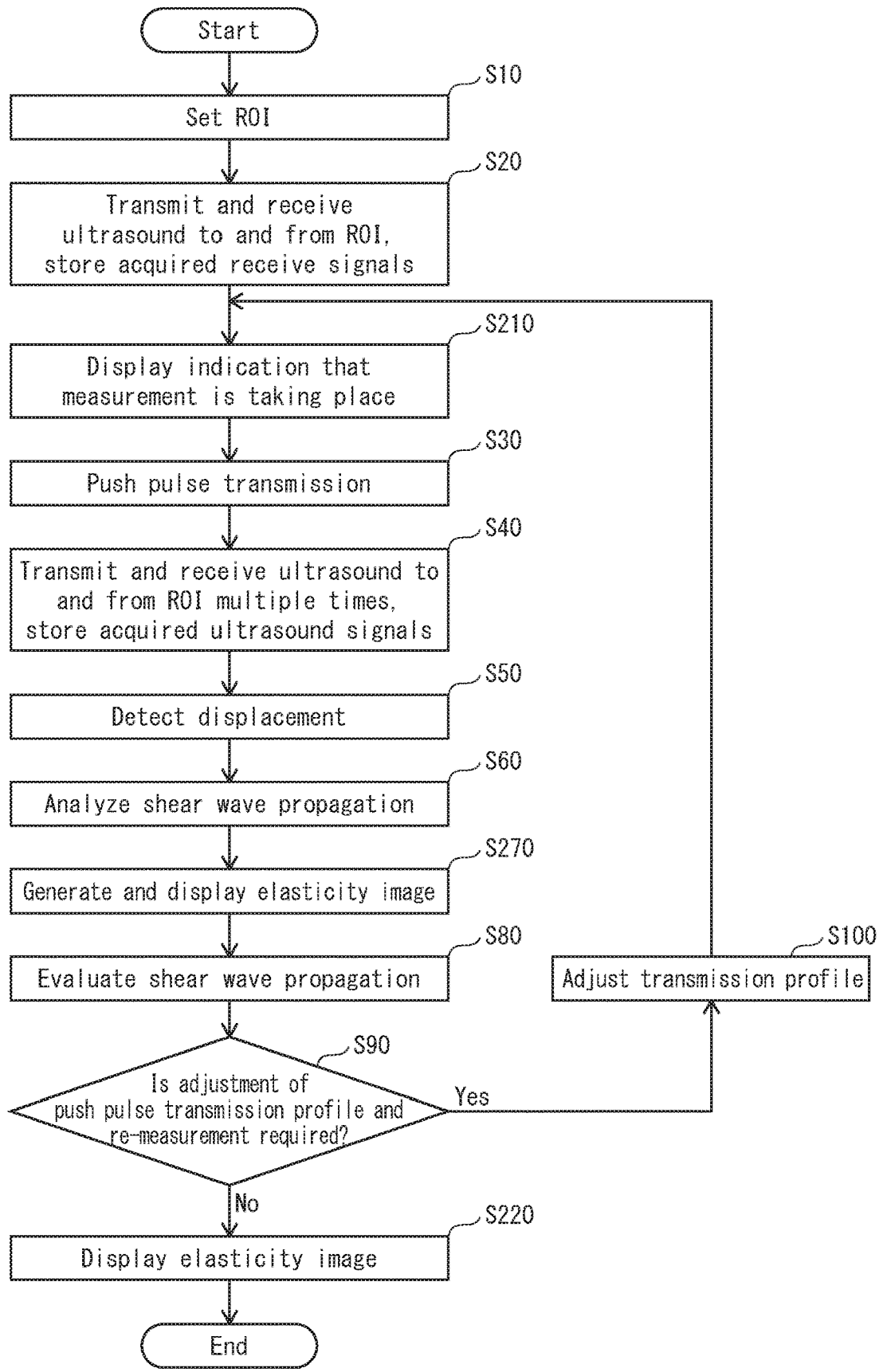
FIG. 11 is a flowchart indicating overall operation of the ultrasound diagnostic device pertaining to Modification 4.

A flowchart pertaining to Modification 4 is shown in FIG. 11. In FIG. 11, operations that are the same as in FIG. 2 are assigned the same step numbers, and description thereof is omitted here.

Figure 12A:
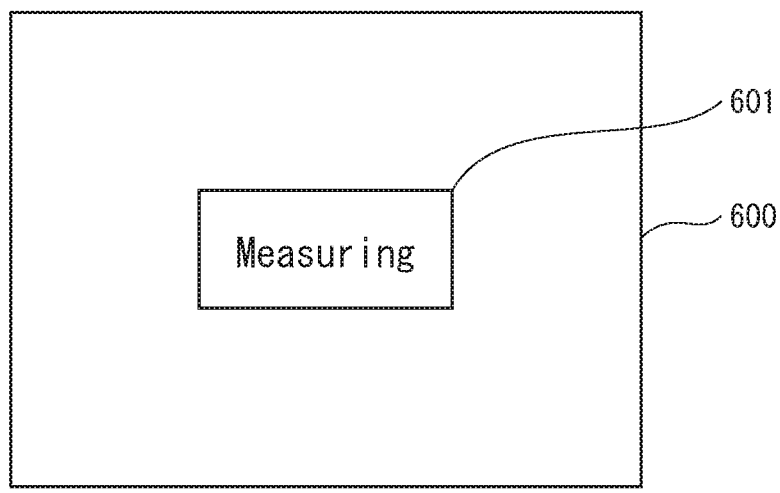
FIGS. 12A and 12B illustrate display examples showing measurement taking place, pertaining to Modification 4.

In step S210, as shown in FIG. 12A, an indication 601 indicating measurement is taking place is outputted to a screen 600 of the display 3.

In step S270, an elasticity image is generated as in step S70, but is not outputted to the display 3.

Further, when the controller determines that re-measuring is not necessary in step S90, the controller outputs the elasticity image generated in the most recent iteration of step S70 to the display 3, instead of the indication that measurement is taking place (step S220).

<Summary>

According to this modification, until it becomes unnecessary to adjust push pulses that generate an elasticity image, an elasticity image is not displayed on the display 3. Accordingly, until an elasticity image is outputted, a user can simply wait while pressing the ultrasound probe against the subject, and can be informed that measurement is completed by the display of an elasticity image.

Note that in step S210 nothing need be outputted to the display 3, and nothing need be outputted to the display 3 in step S270. Accordingly, a user can be informed that measurement is completed by the display of an elasticity image, and therefore until an elasticity image is outputted, a user can simply wait while pressing the ultrasound probe against the subject.

Figure 12B:
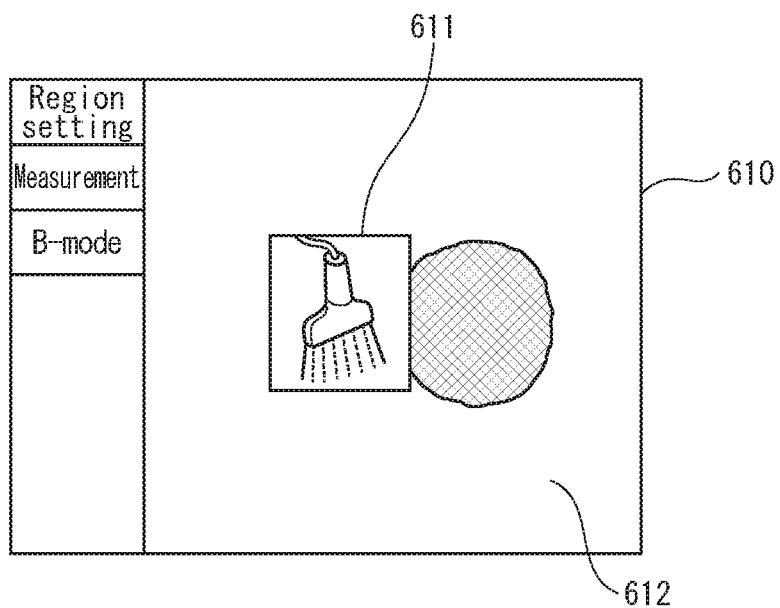

Further, in step S210, an icon such as an icon 611 shown in FIG. 12B may be overlaid on the screen 610 outputted to the display 3, and in step S270, an elasticity image 612 generated as in step S70 may be outputted, and in step S220, display of the icon 611 may be ended. In this way, a user can be notified of the end of measuring by the disappearance of an icon from the screen, and can check the state of acquisition of elasticity images.

Further, step S270 may be performed before step S220 when re-measurement in step S100 does not occur, instead of between steps S60 and S80. Thus, there is no need to generate an elasticity image that isn't displayed. In this case, the elasticity image storage may be omitted.

<<Other Modifications Pertaining to Embodiment>>

(1) According to the Embodiment and modifications, the ultrasound diagnostic device 1 determines a focal point of a push pulse based on an initial value of a transmission profile, and changes or adds to the focal point in response to evaluation of propagation of shear waves. However, a focal point of a push pulse may be adjusted by a user. For example, a focal point of a push pulse may be displayed on the display 3, and a user may change a position of the ultrasound probe 2 or the ultrasound diagnostic device 1 may accept a focal point of a push pulse from a user. A focal point of a push pulse accepted by the ultrasound diagnostic device 1 may be accepted as the focal point itself, or may be, for example, indicate a range in which a focal point can exist. In this way, when a user selects a focal point based on a tomographic image, an elasticity image, etc., a tomographic image can be generated according to conditions selected by the user.

(2) The Embodiment and modifications describe a case in which two or more push pulses are transmitted consecutively with respect to a transmission profile that transmits two or more push pulses. However, sets of push pulse transmission and a plurality of ultrasound transmission and reception may be repeated a number of times equal to the number of push pulses. In this way, shear waves originating from subsequent push pulses will not influence propagation analysis of shear waves originating from an initial push pulse, and therefore hardness measurement can be made more accurate.

(3) The Embodiment and modifications describe a case in which a push pulse transmission profile is adjusted and re-measurement is performed in step S90, steps S30 to S80 are performed using the transmission profile adjusted in step S100, and whether or not to adjust the push pulse transmission profile and perform re-measurement is determined in step S90. However, for example, after the second iteration of steps S30 to S80, measurement may end without performing step S90. In this way, for example, in a case in which any adjustment of transmission profile will not result in a useful propagation analysis due to a positional relationship between the ultrasound probe 2 and the ROI, excessive repetition of push pulse transmission profile adjustment and re-measurement can be avoided. Re-transmission of a push pulse and re-measurement is not limited to one iteration, and a number of iterations may be performed in view of effect on the subject and measurement time, for example three iterations may be performed. In this case, for example, the controller 11 may display the tomographic image of a measurement with the best evaluation according to the evaluator 16 among the initial measurement and all re-measurements.

Further, the evaluator 16 may store evaluation results, and when the result of an evaluation in a second or successive step S90 is not as favorable as the result of an evaluation of a previous step S90, the elasticity image pertaining to the transmission profile of the most favorable result may be displayed and measurement ended. Further, the evaluator may store evaluation results, and a transmission profile may be adjusted based on the most favorable evaluation result stored, while avoiding the same result as the last evaluation result. In this case, adjustment of a transmission profile may be performed if the latest evaluation result does not meet a predefined criteria, and when the latest evaluation result meets the predefined criteria the elasticity image pertaining to the transmission profile of the most favorable evaluation result may be displayed and measurement ended.

(4) The Embodiment and modifications describe a case in which a push pulse transmission profile is adjusted to focus on a region in which shear waves are not propagating, based on a propagation range diagram generated from wavefront images or a propagation range diagram generated from displacement images. However, a push pulse transmission profile may be adjusted without detecting regions in which shear waves do not propagate, for example, based on uniformity of shear wave propagation. For example, a transmission profile may be adjusted to satisfy one or both of (a) and (b), where according to (a) a push pulse focal point is in a region in which shear propagation is uniform, and according to (b) a push pulse focal point is in the vicinity of a region in which shear wave propagation is locally different. Further, when evaluating uniformity of shear waves, evaluation may be performed by using speed and direction of shear waves, as described in the Embodiment, and evaluation may be performed by using tomographic images, as described in Modification 2. Further, when evaluating uniformity of shear wave propagation, an elasticity image may be used. This is because an absolute value of shear wave speed can be evaluated from elasticity values. Accordingly, a region of uniform elasticity can be evaluated as a region of uniform shear wave speed and a region of locally different elasticity can be evaluated as a region of locally different shear wave speeds.

(5) According to Modification 3, the propagation analyzer is described as detecting times at which displacement peaks from displacement images, by using correlation processing. However, the present invention is not limited to this example. For example, a threshold value may be provided with respect to correlation values from correlation processing, and times for which correlation is greater than the threshold value may be detected. In this way, not only peak displacement times are pinpointed, but surrounding times may be detected and therefore wavefronts can be detected more accurately. Further, a minimum threshold value may be provided with respect to correlation values from correlation processing, and a correlation value detected below the minimum threshold value may be detected as not being a peak value. In this way, erroneous detection of oscillation, etc., as a wavefront at times when a wavefront is not passing through can be prevented.

(6) In the Embodiment and modifications is described a case in which, in steps S20 to S40, the ultrasound signal acquirer 13 performs transmission beamforming to make transmitted ultrasound simultaneously arrive at a focal point, and, for each transmission event, performs delay-and-sum on transducer-received signals, and generates an acoustic line signal. However, the present invention is not limited to this example. For example, the ultrasound signal acquirer 13 may make the transducers of the ultrasound probe 2 simultaneously output ultrasound in order to output plane-wave ultrasound. In this case, because there is no need to limit a reception focus point to be near or on the same line as a transmission focus point, acoustic line signals for one tomographic image need not have a one-to-one correspondence with each transmission event, and one image portion can be acquired together. Thus, the framerate of tomographic image signals can be increased, and time resolution with respect to shear wave propagation analysis and speed measurement can be increased. Note that the present invention is not limited to the example methods of transmission beamforming and reception beamforming described. Any form of beamforming that can acquire tomographic images at a framerate that allows acquisition of shear wave propagation states may be performed.

(7) According to the Embodiment and modifications, the displacement detector 14 detects displacement by pattern matching and correlation processing between a tomographic image signal prior to push pulse transmission as a reference tomographic image and tomographic image signals after push pulse transmission, but the present invention is not limited to this example. For example, without performing the tomographic image signal acquisition in step S20, a tomographic image signal capture of the ROI, previously stored in the tomographic image storage 18, or a representative tomographic image signal of the ROI may be used as the reference tomographic image signal. Further, among tomographic image signals after a push pulse, one of two tomographic image signals acquired at different times, separated by a given period of time, may be used as the reference tomographic image signal.

(8) In the Embodiment and modifications is described a case in which the ultrasound signal acquirer 13 generates an acoustic line signal, the tomographic image storage 18 stores the acoustic line signal, and the displacement detector 14 detects displacement by using a tomographic image signal that is one image portion of one or more acoustic line signals. However, the present invention is not limited to this example. For example, the ultrasound signal acquirer 13 may perform a geometric transform for screen display and, using envelope detection, logarithmic compression to result in luminance conversion with respect to a tomographic image signal, and thereby convert a tomographic image signal to tomographic image data which the tomographic image storage 18 stores. In this way, the controller 11 can make the display 3 display the tomographic image data without performing a geometric transform on the elasticity image. Further, the tomographic image data stored by the tomographic image storage 18 need not undergo geometric transform and luminance conversion by logarithmic compression, and can be displayed by the display 3 as is.

(9) According to the Embodiment and Modifications 1, 2, and 4, the propagation analyzer 15 extracts displacement regions with respect to an entirety of a displacement image, but the present invention is not limited to this example. For example, the propagation analyzer 15 may extract displacement regions only in the vicinity of a push pulse application point, with respect to a displacement image immediately after push pulse application. In this way, calculation load can be decreased and regions in which shear waves are obviously not present are not extracted and therefore erroneous detection of noise as wavefronts can be avoided. Limiting the range of the extraction of displacement regions is not limited to this example. For example, when no shear waves are detected at a given y coordinate, the y coordinate may be removed from an extraction range of displacement positions at subsequent times.

Further, in a similar way, the propagation analyzer 15 may perform time filtering processing based on push pulse application times. For example, wavefronts that are not in the vicinity of a push pulse application point in a wavefront image immediately after push pulse application may be eliminated as noise. In this way, erroneous detection as wavefronts of noise in regions in which shear waves are clearly not present can be avoided.

Further, the propagation analyzer 15 need not perform spatial filtering processing and time filtering processing in a specific order, and may perform them simultaneously.

(10) According to Modification 3, the propagation analyzer 15 is described as detecting times at which displacement peaks from displacement images, by using correlation processing. However, the present invention is not limited to this example. For example, a threshold value may be provided with respect to correlation values from correlation processing, and times for which correlation is greater than the threshold value may be detected. In this way, not only peak displacement times are pinpointed, but surrounding times may be detected and therefore wavefronts can be detected more accurately. Further, a minimum threshold value may be provided with respect to correlation values from correlation processing, and a correlation value detected below the minimum threshold value may be detected as not being a peak value. In this way, erroneous detection of oscillation, etc., as a wavefront at times when a wavefront is not passing through can be prevented.

(11) According to the Embodiment and modifications, the ultrasound diagnostic device is connected to the display 3, but the present invention is not limited to this example. For example, the ultrasound diagnostic device 1 may include the display 3, or the ultrasound diagnostic device 1 may store in another storage medium or output to another device via a network the elasticity image data generated by the propagation analyzer 15 and stored in the elasticity image storage 21, without being connected to the display 3.

Further, similarly, the ultrasound diagnostic device may include the ultrasound probe 2, or the ultrasound probe 2 may include the ultrasound signal acquirer 13 and an ultrasound diagnostic device that does not include the ultrasound signal acquirer 13 may acquire acoustic line signals from the ultrasound probe 2.

(12) All elements or a portion of the elements of the ultrasound diagnostic device pertaining to the Embodiment and modifications may be implemented as an integrated circuit on single chip or a plurality of chips, may be implemented as a computer program, and may be implemented in other formats. For example, the propagation analyzer and the evaluator may be implemented as a single chip, the ultrasound signal acquirer may be implemented as a single chip, and the displacement detector and other elements may be implemented as another chip.

When implemented as an integrated circuit, the elements are typically implemented as a large scale integration (LSI). Here, an LSI may refer to an integrated circuit, a system LSI, a super LSI, or an ultra LSI, depending on the level of integration.

Further, methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the functional blocks.

Further, the ultrasound diagnostic device pertaining to the Embodiment and modifications may be implemented as a program stored on a storage medium and a computer that reads and executes the program. The storage medium may be any kind of storage medium, such as a memory card or CD-ROM. Further, the ultrasound diagnostic device pertaining to the present invention may be implemented as program downloadable via a network and a computer that downloads and executes the program.

(13) The Embodiment described above is an example of a preferred embodiment of the present invention. The values, shapes, materials, component elements, positions and connections of the component elements, processes, ordering of processes, etc., are only examples and are not intended to limit the scope of the present invention. Further, among the component elements of the Embodiment, processes not recited in the independent claims that indicate highest level concepts of the present invention are described as optional elements to improve on the highest level concepts.

Further, in order to aid understanding of the invention, the dimensions of the elements illustrated in the drawings for the Embodiment may differ from actual dimensions. Further, the present invention is not intended to be limited in scope by the Embodiment, and can be appropriately modified without departing from the scope of the present invention.

Further, in the ultrasound diagnostic device are members such as circuit elements and lead lines on substrates, but description thereof is omitted, as various configurations are possible based on common knowledge in the technical fields of electrical wiring and circuitry, and such description is not directly relevant to the present invention. The drawings are schematic diagrams, and are not necessarily exact.

<<Supplement>>

(1) The ultrasound diagnostic device pertaining to the embodiment is an ultrasound diagnostic device that uses an ultrasound probe to transmit a push pulse of focused ultrasound to a focal point in a subject to physically push tissue at the focal point, after which the ultrasound probe is used to repeatedly transmit and receive ultrasound to detect propagation, in a region of interest (ROI), of shear waves that originate from the pushed tissue at the focal point, the ultrasound diagnostic device comprising: an ultrasound signal processing circuit, the ultrasound signal processing circuit comprising: a push pulse transmitter that transmit the push pulse based on a transmission profile; a displacement detector that repeatedly transmits ultrasound into the subject after the push pulse, receives reflected ultrasound from the subject that corresponds to transmitted ultrasound in order to acquire a time series of receive signals, and detects displacement due to shear waves in tissue in the ROI that are caused by the push pulse; an evaluator that evaluates shear wave propagation in the ROI, based on detection results from the displacement detector; and a push pulse adjuster that adjusts the transmission profile, based on evaluation results from the evaluator, wherein when the push pulse adjuster adjusts the transmission profile, the push pulse transmitter transmits a second push pulse based on the adjusted transmission profile, and the displacement detector detects displacement due to shear waves that are caused by the second push pulse.

Furthermore, the ultrasound diagnostic device control method pertaining to the embodiment is a control method for controlling an ultrasound diagnostic device that uses an ultrasound probe to transmit a push pulse of focused ultrasound to a focal point in a subject to physically push tissue at the focal point, after which the ultrasound probe is used to repeatedly transmit and receive ultrasound to detect propagation, in a region of interest (ROI), of shear waves that originate from the pushed issue at the focal point, the control method comprising: transmitting the push pulse based on a transmission profile; repeatedly transmitting ultrasound into the subject after the push pulse; receiving reflected ultrasound from the subject that corresponds to transmitted ultrasound in order to acquire a time series of receive signals; detecting displacement due to shear waves in tissue in the ROI that are caused by the push pulse; evaluating shear wave propagation in the ROI, based on results of the detecting displacement due to shear waves; and adjusting the transmission profile, based on results of the evaluating shear wave propagation, wherein when the adjusting the transmission profile is performed a second push pulse is transmitted, based on the adjusted transmission profile, and displacement due to shear waves that are caused by the second push pulse is detected.

According to the present disclosure and the above configuration, a transmission profile can be optimized, the transmission profile controlling a push position and energy of a push pulse based on propagation of shear waves. Thus when tissue hardness measurement accuracy in a subject is decreased due to reflection, refraction, or attenuation of shear waves, or measurement is not possible, the transmission profile can be optimized and measurement re-taken to obtain results. Accordingly, when tissue hardness measurement accuracy in a subject is decreased or measurement is not possible, the complexity of trial and error can be reduced, when the trial and error involves a user estimating causes and adjusting the transmission profile based on the estimation, in order to re-take measurements. Thus, it is possible to perform hardness measurement of tissue with high accuracy in a way that is simple for a user.

(2) The ultrasound diagnostic device of (1) may further comprise: a propagation analyzer that analyzes shear wave propagation in the ROI, using displacement of tissue in the ROI that corresponds to the time series of the receive signals detected by the displacement detector, wherein the evaluator evaluates the shear wave propagation in the ROI based on analysis results from the propagation analyzer.

According to this configuration, evaluation of shear wave propagation and optimization of a push pulse transmission profile can be performed based on results of analysis of shear wave direction, speed, propagation range, etc.

(3) The ultrasound diagnostic device of (2) may be configured so the propagation analyzer calculates propagation speed of shear waves at points in the ROI that correspond to the time series of the receive signals, based on the detection results from the displacement detector.

According to this configuration, evaluation of shear wave propagation and optimization of a push pulse transmission profile can be performed based on shear wave speed at each time.

(4) The ultrasound diagnostic device of any one of (1) to (3) may be configured so the evaluator evaluates shear wave propagation in the ROI by using displacement of tissue in the ROI that corresponds to the time series of the receive signals detected by the displacement detector.

According to this configuration, evaluation of shear wave speed, direction, and propagation can be performed based directly on the displacement of tissue.

(5) The ultrasound diagnostic device of (4) may be configured so the evaluator evaluates whether or not shear waves are propagating, based on presence or absence of displacement, for each point in the ROI at each time in the time series of the receive signals.

According to this configuration, evaluation of shear wave propagation range can be performed without performing shear wave propagation analysis.

(6) The ultrasound diagnostic device of any one of (1) to (5) may be configured so the transmission profile includes at least one control parameter, wherein the focal point of a push pulse, a duration of a push pulse, a number of transducers of the ultrasound probe used in transmission of a push pulse, and a number of push pulse transmissions are control parameters, and the push pulse adjuster changes at least one control parameter of the at least one control parameter when adjusting the transmission profile.

(7) The ultrasound diagnostic device of (6) may be configured so the control parameters further include focal depth of a push pulse and direction and angle of propagation of a push pulse relative to the ultrasound probe.

According to these configurations, push pulse focal point, push pulse energy, and the number of push pulse focal points can be adjusted.

(8) The ultrasound diagnostic device of (6) or (7) may be configured so when the number of push pulse transmissions is changed from one to two, the push pulse adjuster selects two different focal points in the subject, selecting one to be the focal point of push pulse number one and the other to be the focal point of push pulse number two.

According to this configuration, shear wave propagation range can be increased while controlling other effects on subject tissue, without increasing the energy of each push pulse.

(9) The ultrasound diagnostic device of any one of (1) to (7) may be configured so the evaluator evaluates whether or not shear waves are propagating in the ROI, and when the evaluator determines that a region exists in the ROI in which shear wave propagation is not present, the push pulse adjuster adjusts the transmission profile to cause a shear wave to reach the region.

According to this configuration, a push pulse can be transmitted in a way that causes shear waves to propagate across the entirety of an ROI, and that suppresses the occurrence of regions in which elasticity cannot be acquired.

(10) The ultrasound diagnostic device of (9) may be configured so, when shear wave propagation is present in only one of a shallower region and a deeper region of the ROI than the region in which shear wave propagation is not present, the push pulse adjuster moves the focal point of a push pulse closer to the region in which shear wave propagation is not present.

According to this configuration, transmission of a push pulse can be adjusted in a way that causes shear waves to propagate across the entirety of an ROI, for example when a depth of a push pulse focal point is not appropriate.

(11) The ultrasound diagnostic device of (9) may be configured so, when shear wave propagation is present in both a shallower region and a deeper region of the ROI than the region in which shear wave propagation is not present, the push pulse adjuster moves the focal point of a push pulse in a transducer array direction of the ultrasound probe.

According to this configuration, transmission of a push pulse can be adjusted in a way that causes shear waves to propagate across the entirety of an ROI, for example when a non-propagation region occurs due to shear wave refraction, etc.

(12) The ultrasound diagnostic device of (9) may be configured so, when, in a transducer array direction of the ultrasound probe, the region in which shear wave propagation is not present includes one end of the ROI and does not include the other end of the ROI, the push pulse adjuster increases energy of a push pulse and/or adds a focal point for an additional push pulse inside or in the vicinity of the region in which shear wave propagation is not present.

According to this configuration, transmission of a push pulse can be adjusted in a way that causes shear waves to propagate across the entirety of an ROI, for example when attenuation occurs in shear wave propagation.

(13) The ultrasound diagnostic device of (9) may be configured so, when, in a transducer array direction of the ultrasound probe, the region in which shear wave propagation is not present is sandwiched between regions in which shear wave propagation is present, the push pulse adjuster adds a focal point for an additional push pulse in the vicinity of the region in which shear wave propagation is not present.

According to this configuration, transmission of a push pulse can be adjusted in a way that causes shear waves to propagate across the entirety of an ROI, for example when interference occurs between a reflected shear wave and a propagating shear wave or when shear waves do not propagate into a reflection origin.

(14) The ultrasound diagnostic device of any one of (1) to (13) may be configured so the evaluator evaluates uniformity of shear wave propagation in the ROI, and the push pulse adjuster adjusts the transmission profile to adjust the focal point of a push pulse to be in a region in which shear waves uniformly propagate.

According to this configuration, occurrence of shear wave refraction and reflection can be suppressed and the accuracy of shear wave speed measurement increased.

(15) The ultrasound diagnostic device of any one of (1) to (14) may be configured so the evaluator evaluates uniformity of shear wave propagation in the ROI, and the push pulse adjuster adjusts the transmission profile to adjust the focal point of a push pulse to be in the vicinity of a region in which shear wave propagation is locally differentiated.

According to this configuration, accuracy of elasticity measurement can be increased with respect to tissue that has a varying elasticity range (e.g. a tumor), which corresponds to a region in which shear wave propagation is locally differentiated.

(16) The ultrasound diagnostic device of any one of claims (1) to (15) may further comprise an elasticity measurer that measures elasticity of tissue in the subject, based on detection results from the displacement detector.

According to this configuration, elasticity of tissues in a subject can be measured based on push pulse transmission.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included herein.

What is claimed is:

1. An ultrasound diagnostic device that uses an ultrasound probe to transmit a push pulse of focused ultrasound to a focal point in a subject to physically push tissue at the focal point, after which the ultrasound probe is used to repeatedly transmit and receive ultrasound to detect propagation, in a region of interest (ROI), of shear waves that originate from the pushed tissue at the focal point, the ultrasound diagnostic device comprising:
   an ultrasound signal processing circuit, the ultrasound signal processing circuit comprising:
      a push pulse transmitter that that is configured to transmit, as the push pulse, a first push pulse to a first focal point, based on a transmission profile, wherein the transmission profile is an information profile which defines at least one control parameter for transmitting the push pulse;
      a displacement detector that is configured to repeatedly transmit ultrasound into the subject after the first push pulse, receives reflected ultrasound from the subject that corresponds to transmitted ultrasound in order to acquire a time series of receive signals, and detect displacement due to shear waves in tissue in the ROI that are caused by the first push pulse;
      an evaluator that is configured to evaluate shear wave propagation in the ROI, based on detection results from the displacement detector; and
      a push pulse adjuster that is configured to adjust the transmission profile, based on evaluation results from the evaluator,
   wherein the push pulse transmitter is further configured to transmit, as the push pulse, a subsequent push pulse based on the adjusted transmission profile which is adjusted by the push pulse adjuster, and the displacement detector is configured to detect displacement due to shear waves that are caused by the subsequent push pulse,
   wherein the evaluator is configured to evaluate whether or not shear waves are propagating in the ROI, and the push pulse adjuster is configured to adjust the transmission profile to cause a shear wave to reach a region in the ROI in which shear wave propagation has been determined not to be present by the evaluator,
   wherein in a case in which the evaluator determines that the region in which shear wave propagation is not present includes a first end of the ROI in a transducer array direction of the ultrasound probe and does not include a second end of the ROI in the transducer array direction, the push pulse adjuster increases energy of the subsequent push pulse, and
   wherein the evaluator is further configured to evaluate uniformity of shear wave propagation in the ROI caused by the first push pulse, and, in a case in which the evaluator identifies, based on the evaluation of uniformity, a first region in the-ROI in which shear wave propagation is uniform and a second region in the ROI in which shear wave propagation is locally differentiated, the push pulse adjuster adjusts is configured to adjust the transmission profile to set a focal point of the subsequent push pulse to be at a location that is within the first region in which shear wave propagation is uniform and that is closer to, but not inside of, the second region in which shear wave propagation is locally differentiated, and that is closer to, but not inside of, the region in which shear wave propagation is not present, as compared to a location of the first focal point of the first push pulse that was previously transmitted and that generated the shear waves on which the evaluation was based.

2. The ultrasound diagnostic device of claim 1, wherein the ultrasound signal processing circuit further comprises:
   a propagation analyzer that is configured to analyze shear wave propagation in the ROI, using displacement of tissue in the ROI that corresponds to the time series of the receive signals detected by the displacement detector,
   wherein the evaluator is configured to evaluate the shear wave propagation in the ROI based on analysis results from the propagation analyzer.

3. The ultrasound diagnostic device of claim 2, wherein the propagation analyzer is configured to calculate propagation speed of shear waves at points in the ROI that correspond to the time series of the receive signals, based on the detection results from the displacement detector.

4. The ultrasound diagnostic device of claim 1, wherein the evaluator is configured to evaluate shear wave propagation in the ROI, by using displacement of tissue in the ROI that corresponds to the time series of the receive signals detected by the displacement detector.

5. The ultrasound diagnostic device of claim 4, wherein the evaluator is configured to evaluate whether or not shear waves are propagating, based on presence or absence of displacement, for each point in the ROI at each time in the time series of the receive signals.

6. The ultrasound diagnostic device of claim 1,
   wherein the transmission profile includes at least one control parameter,
   wherein the at least one control parameter includes at least one of (i) the focal point of a push pulse, (ii) a duration of a push pulse, (iii) a number of transducers of the ultrasound probe used in transmission of a push pulse, and (iv) a number of push pulse transmissions, and
   the push pulse adjuster is configured to adjust the transmission profile by changing at least one control parameter of the at least one control parameter of the transmission profile.

7. The ultrasound diagnostic device of claim 6, wherein the at least one control parameter further includes focal depth of a push pulse and direction and angle of propagation of a push pulse relative to the ultrasound probe.

8. The ultrasound diagnostic device of claim 6,
   wherein the at least one control parameter includes the focal point of the push pulse, and the number of push pulse transmissions, and
   wherein the push pulse adjuster adjusts the transmission profile by changing the number of push pulse transmissions from one to two such that the subsequent push pulse includes a first subsequent push pulse and a second subsequent push pulse, and selecting two different focal points in the subject, wherein the push pulse adjuster selects one of the two different focal points to be the focal point of the first subsequent push pulse and the other of the two different focal points to be the focal point of the second subsequent push pulse.

9. The ultrasound diagnostic device of claim 1, wherein in a case in which the evaluator determines that shear wave propagation is present in only one of a shallower region and a deeper region of the ROI than the region in which shear wave propagation is not present, the push pulse adjuster moves a the focal point of the subsequent push pulse along a depth direction closer to the region in which shear wave propagation is not present.

10. The ultrasound diagnostic device of claim 1, wherein in a case in which the evaluator determines that shear wave propagation is present in both a shallower region and a deeper region of the ROI than the region in which shear wave propagation is not present, the push pulse adjuster moves the focal point of the subsequent push pulse in the transducer array direction of the ultrasound probe.

11. The ultrasound diagnostic device of claim 1, wherein in the case in which the evaluator determines that the region in which shear wave propagation is not present includes the first end of the ROI in the transducer array direction of the ultrasound probe and does not include the second end of the ROI in the transducer array direction, the push pulse adjuster adds a focal point for an additional subsequent push pulse inside or in a vicinity of the region in which shear wave propagation is not present.

12. The ultrasound diagnostic device of claim 1, wherein in a case in which the evaluator determines that the region in which shear wave propagation is not present is sandwiched between regions in which shear wave propagation is present along a transducer array direction of the ultrasound probe, the push pulse adjuster adds a focal point for an additional subsequent push pulse in a vicinity of the region in which shear wave propagation is not present.

13. The ultrasound diagnostic device of claim 1, further comprising:
   an elasticity measurer that measures elasticity of tissue in the subject, based on detection results from the displacement detector.

14. A control method for controlling an ultrasound diagnostic device that uses an ultrasound probe to transmit a push pulse of focused ultrasound to a focal point in a subject to physically push tissue at the focal point, after which the ultrasound probe is used to repeatedly transmit and receive ultrasound to detect propagation, in a region of interest (ROI), of shear waves that originate from the pushed tissue at the focal point, the control method comprising:
   transmitting, as the push pulse, a first push pulse to a first focal point, based on a transmission profile, wherein the transmission profile is an information profile which defines at least one control parameter for transmitting the push pulse;
   repeatedly transmitting ultrasound into the subject after the first push pulse;
   receiving reflected ultrasound from the subject that corresponds to transmitted ultrasound in order to acquire a time series of receive signals;
   detecting displacement due to shear waves in tissue in the ROI that are caused by the first push pulse;
   evaluating shear wave propagation in the ROI, based on results of the detecting displacement due to shear waves; and
   adjusting the transmission profile, based on results of the evaluating shear wave propagation,
   wherein a subsequent push pulse is transmitted as the push pulse, based on the adjusted transmission profile, and displacement due to shear waves that are caused by the second subsequent push pulse is detected,
   wherein the evaluating comprises evaluating whether or not shear waves are propagating in the ROI, and the adjusting the transmission profile comprises adjusting the transmission profile to cause a shear wave to reach a region in the ROI in which shear wave propagation has been determined not to be present by the evaluating,
   wherein in a case in which it is determined in the evaluating that the region in which shear wave propagation is not present includes a first end of the ROI in a transducer array direction of the ultrasound probe and does not include a second end of the ROI in the transducer array direction, the adjusting the transmission profile comprises increasing energy of the subsequent push pulse, and
   wherein the evaluating further comprises evaluating uniformity of shear wave propagation in the ROI, and, in a case in which, based on the evaluation of uniformity, a first region is identified in the ROI in which shear wave propagation is uniform and a second region is identified in the ROI in which shear wave propagation is locally differentiated, the adjusting the transmission profile comprises adjusting the transmission profile to set a focal point of the subsequent push pulse to be at a location that is within the first region in which shear wave propagation is uniform and that is closer to, but not inside of, the second region in which shear wave propagation is locally differentiated, and that is closer to, but not inside of, the region in which shear wave propagation is not present, as compared to a location of the first focal point of the first push pulse that was previously transmitted and that generated the shear waves on which the evaluation was based.

* * * * *